(12) United States Patent  
Plaetinck et al.

(10) Patent No.: US 7,358,069 B2
(45) Date of Patent: Apr. 15, 2008

(54) VECTOR CONSTRUCTS

(75) Inventors: Geert Plaetinck, Merelbeke (BE); Jean-pierre Renard, Gentbrugge (BE); Thierry Bogaert, Kortrijk (BE)

(73) Assignee: Devgen N.V., Zwijnaarde (BE)

( * ) Notice: Subject to any disclaimer, the term of this patent is extended or adjusted under 35 U.S.C. 154(b) by 426 days.

(21) Appl. No.: 09/860,763

(22) Filed: May 18, 2001

(65) Prior Publication Data

US 2004/0166580 A1 Aug. 26, 2004

(30) Foreign Application Priority Data

May 19, 2000 (GB) .................................. 0012233.3

(51) Int. Cl.
*C12P 19/34* (2006.01)
(52) U.S. Cl. .............. 435/91.3; 435/320.1; 435/252.33
(58) Field of Classification Search ..................... 435/6, 435/320.1, 325

See application file for complete search history.

(56) References Cited

U.S. PATENT DOCUMENTS

| 4,766,072 | A |   | 8/1988 | Jendrisak et al. |
|---|---|---|---|---|
| 5,017,488 | A |   | 5/1991 | McAllister et al. |
| 5,882,642 | A | * | 3/1999 | Choi et al. ................ 424/93.21 |
| 5,955,363 | A |   | 9/1999 | Lewis et al. |
| 6,610,529 | B1 | * | 8/2003 | Curtiss et al. ........... 435/252.3 |

FOREIGN PATENT DOCUMENTS

| FR |   | 2782325 A |   | 2/2000 |
| WO |   | WO00/01846 | * | 1/2000 |
| WO |   | WO 00/01846 A2 |   | 1/2000 |
| WO |   | WO 01/34815 A1 |   | 5/2001 |

OTHER PUBLICATIONS

NEB Catalog 1996-1997.*
Simcox, T.G. Gene Srfl, a new type-II restriction endonuclease that recognizes the octanucleotide sequence Dec. 20, 1991; 109(1):121-123.*
No author, *Promega Life Science Catalogue*, pp. 13.6-13.7 (2000).
Jeng.et al., *Can. J. Microbiol.* 43: 1147-1156 (1997).

* cited by examiner

*Primary Examiner*—James Ketter
(74) *Attorney, Agent, or Firm*—Wolf, Greenfield & Sacks, P.C.

(57) ABSTRACT

Improved vector constructs useful in the expression of double-stranded RNA are provided. The constructs are particularly useful for expression of double-stranded RNA in vitro and in vivo.

28 Claims, 18 Drawing Sheets (a): promoter 1
(b): promoter 2

(e): Terminator 1
(f): Terminator 2

FIG. 2.
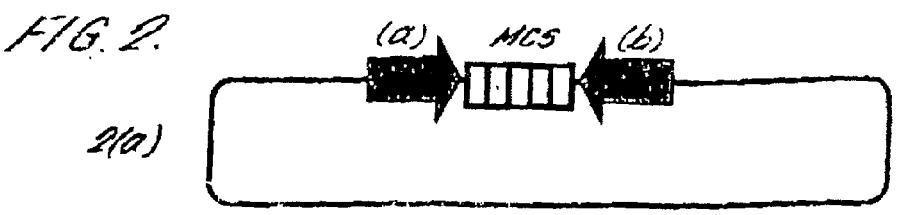
2(a)
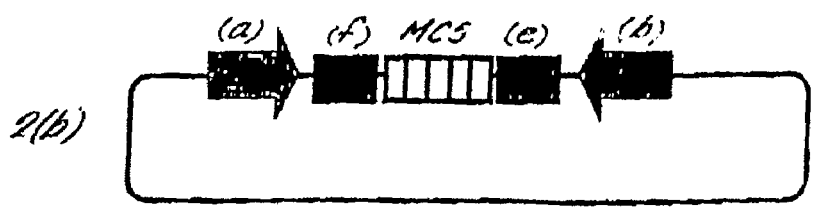
2(b)
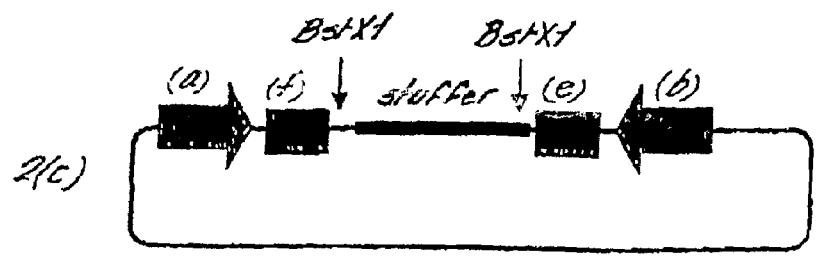
2(c)
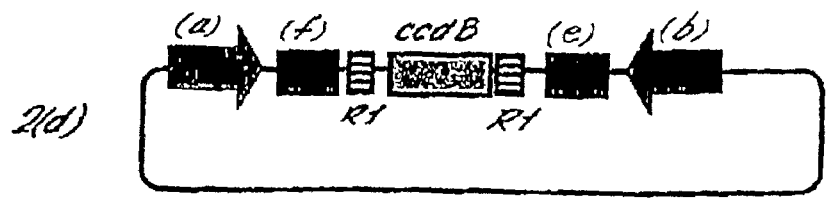
2(d)
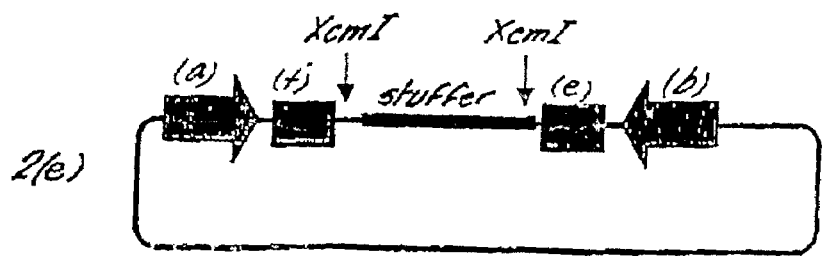
2(e)
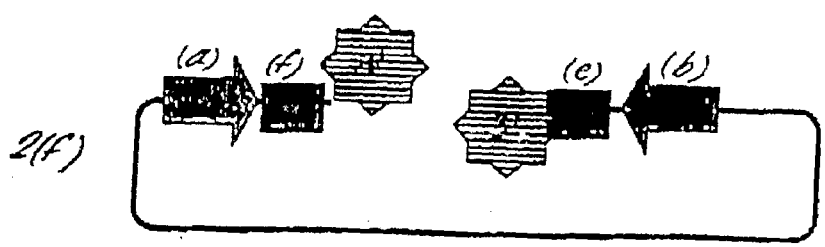
2(f)

Construction RNAi vector with T7 terminators

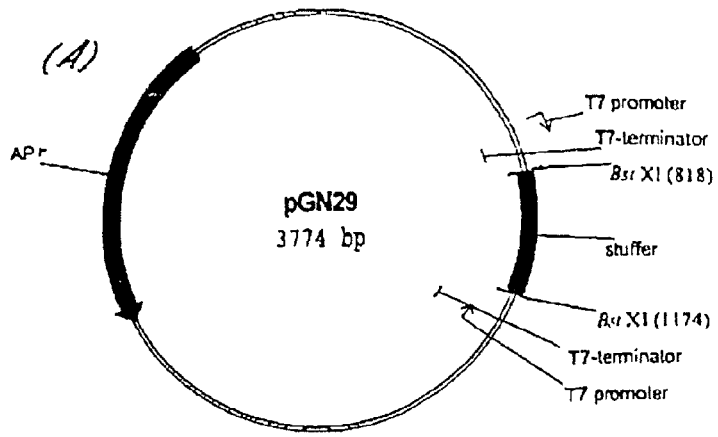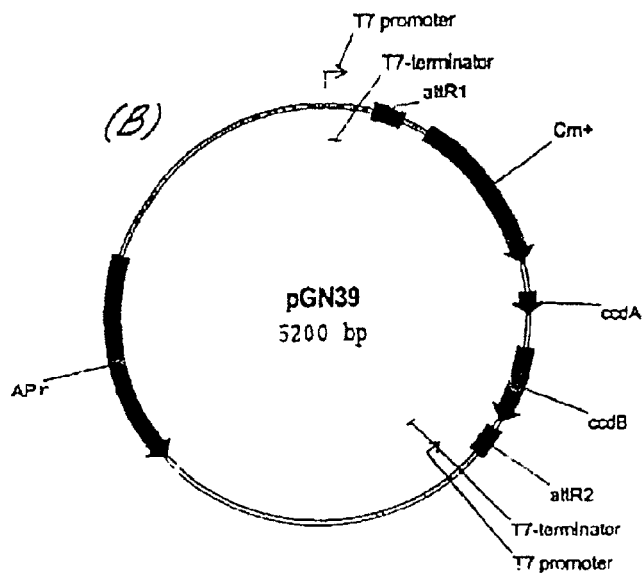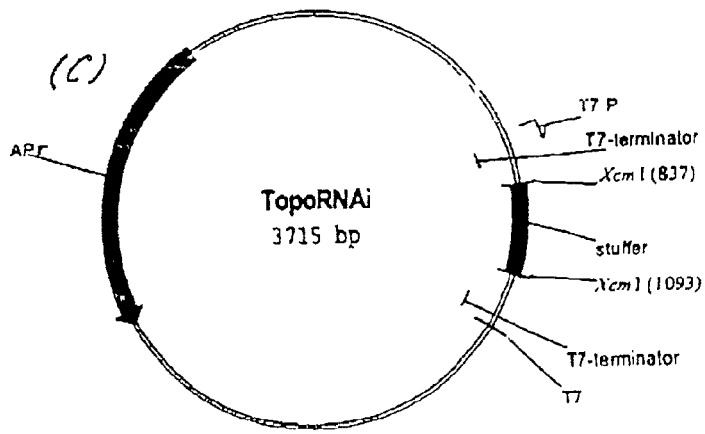
FIG. 9.

FIG. 10.

pGN9

```
   1 gagtgcacca tatgcggtgt gaaataccgc acagatgcgt aaggagaaaa taccgcatca
  61 ggcgaaattg taaacgttaa tattttgtta aaattcgcgt taaatatttg ttaaatcagc
 121 tcattttttta accaataggc cgaaatcggc aaaatccctt ataaatcaaa agaatagacc
 181 gagataggqt tgagtgttgt tccagtttgg aacaagagtc cactattaaa gaacgtggac
 241 tccaacgtca aagggcgaaa aaccgtctat cagggcgatg gcccactacg tgaaccatca
 301 cccaaatcaa gtttttgcg gtcgaggtgc cgtaaagctc taaatcggaa ccctaaaggg
 361 agccccgat ttagagcttg acggggaaag ccggcgaacg tggcgagaaa ggaagggaag
 421 aaagcgaaag gagcgggcgc tagggcgctg gcaagtgtag cggtcacgct gcgcgtaacc
 481 accacaccg ccgcgcttaa tgcgccgcta cagggcgcgt ccattcgcca ttcaggctgc
 541 gcaactgttg ggaagggcga tcggtgcggg cctcttcgct attacgccag ctggcgaaag
 601 ggggatgtgc tgcaaggcga ttaagttggg taacgccagg gttttcccag tcacgacgtt
 661 gtaaaacgac ggccagtgaa tgtaatacg actcactata gggcgaattc aaaaaacccc
 721 tcaagacccg tttagaggcc caaggggtt atgctagtga attctgcagg gtaccgggg
 781 atcctctaga cgcgtaagct tactagcata acccttgg gcctctaaac gggtcttgag
 841 gggttttttg agcttctcgc cctatagtga gtcgtattac agcttgagta ttctatagtg
 901 tcacctaaat agcttggcgt aatcatggtc atagctgttt cctgtgtgaa attgttatcc
 961 gctcacaatt ccacacaaca tacgagccgg aagcataaag tgtaagcct gggtgccta
1021 atgagtgagc taactcacat taattgcgtt gcgctcactg cccgctttcc agtcgggaaa
1081 cctgtcgtgc cagctgcatt aatgaatcgg ccaacgcgcg gggagaggcg gtttgcgtat
1141 tgggcgctct tccgcttcct cgctcactga ctcgctgcgc tcggtcgttc ggctgcggcg
1201 agcggtatca gctcactcaa aggcggtaat acggttatcc acagaatcag gggataacgc
1261 aggaaagaac atgtgagcaa aaggccagca aaagccagg aaccgtaaaa aggccgcgtt
1321 gctggcgttt ttcgatagc tccgccccc tgacgagcat cacaaaaatc gacgctcaag
1381 tcagaggtgg cgaaacccga caggactata agcgttteccc ccgaagctc
1441 cctcgtgcgc tctcctgttc cgaccctgcc gcttaccgga tacctgtccg cctttctccc
1501 ttcgggaagc gtggcgcttt ctcatagctc acgctgtagg tatctcagtt cggtgtaggt
1561 cgttcgctc aagctgggct gtgtgcacga accccccgtt cagcccgacc gctgcgcctt
1621 atccggtaac tatcgtcttg agtccaacce ctggtaagac gacttatcgc cactggcagc
1681 agccactggt aacaggatta gcagagcgag gtatgtaggc ggtgctacag agttcttgaa
1741 gtggtggcct aactacggct acactagaag gacagtattt ggtatctgcg ctctgctgaa
1801 gccagttacc ttcggaaaaa gagttggtag ctcttgatcc ggcaaacaaa ccaccgctgg
1861 tagcggtggt ttttttgttt gcaagcagca gattacgcgc agaaaaaaag gatctcaaga
1921 agatcctttg atcttttcta cggggtctga cgctcagtgg aacgaaaact cacgttaagg
1981 gattttggtc atgagattat caaaaaggat cttcacctag atccttttaa attaaaaatg
2041 aagttttaaa tcaatctaaa gtatatatga gtaaacttgg tctgacagtt accaatgctt
2101 aatcagtgag gcacctatct cagcgatctg tctatttcgt tcatccatag ttgcctgact
2161 ccccgtcgtg tagataacta cgatacggga gggcttacca tctggcccca gtgctgcaat
2221 gataccgcga gacccacgct caccggctcc agatttatca gcaataaacc agccagccgg
2281 aagggccgag cgcagaagtg gtcctgcaac tttatccgcc tccatccagt ctattaattg
2341 ttgccgggaa gctagagtaa gtagttcgcc agttaatagt ttgcgcaacg ttgttgccat
2401 tgctacaggc atcgtggtgt cacgctcgtc gtttggtatg gcttcattca gctccggttc
2461 ccaacgatca aggcgagtta catgatcccc catgttgtgc aaaaaagcgg ttagctcctt
2521 cggtcctccg atcgttgtca gaagtaagtt ggccgcagtg ttatcactca tggttatggc
2581 agcactgcat aattctctta ctgtcatgcc atccgtaaga tgcttttctg tgactggtga
2641 gtactcaacc aagtcattct gagaataccg cgccggcga ccgagttgct cttgcccggc
2701 gtcaatacgg gataatagtg tatgacatag cagaactta aaagtgctca tcattggaaa
2761 acgttcttcg gggcgaaaac tctcaaggat cttaccgctg ttgagatcca gttcgatgta
2821 acccactcgt gcacccaact gatcttcagc atcttttact ttcaccagcg tttctgggtg
2881 agcaaaaaca ggaaggcaaa atgccgcaaa aaagggaata agggcgacac ggaaatgttg
2941 aatactcata ctcttccttt ttcaatatta ttgaagcatt tatcagggtt attgtctcat
3001 gagcggatac atatttgaat gtatttagaa aaataaacaa ataggggttc cgcgcacatt
3061 tccccgaaaa gtgccacctg acgtctaaga aaccattatt atcatgacat taacctataa
3121 aaataggcgt atcacgaggc cctttcgtct cgcgcgtttc ggtgatgacg gtgaaaacct
3181 ctgacacatg cagctcccgg agacggtcac agcttgtctg taagcggatg ccgggagcag
3241 acaagcccgt cagggcgcgt cagcgggtgt tggcgggtgt cggggctggc ttaactatgc
3301 ggcatcagag cagattgtac tga
```

FIG. 11.

PGN29

```
   1 gagtgcauca tatgcggtgt gaaataccgc acagatgcgt aaggagaaaa taccgcatca
  61 ggcgaaattg taaacgttaa tattttgtta aaattcgcgt taaatatttg ttaaatcagc
 121 tcatttttta accaataggc cgaaatcggc aaaatcactt ataaatcaaa agaatagacc
 181 gagataggqt tgagtgttgt tccagtttgg aacaagagtc cactattaaa gaacgtggac
 241 tccaacgtca aaqqgcgaaa aaccgtctat caggqcgatg gcccactacg tgaaccatca
 301 cccaaatcaa gtttttttgcg gtcgaggtgc cgtaaagctc taaatcggaa ccctaaaggg
 361 agccccgat ttagagcttg acggggaaag ccggcgaacg tggcgagaaa ggaagggaag
 421 aaagcgaaag gagcgggcgc tagggcgctg gcaagtgtag cggtcacgct gcgcgtaacc
 481 accacaccqg ccgcgcttaa tgcgccgcta cagggcgcgt ccattcgcca ttcaggctgc
 541 gcaactgttg ggaagggcga tcggtgcggg cctcttcgct attacgccag ctggcgaaag
 601 ggggatgtgc tgcaaggcga ttaagttggg taacgccagg gttttcccag tcacgacgtt
 661 gtaaaacgac ggccagtgaa ttgtaatacg actcactata gggcgaattc aaaaaacccc
 721 tcaagacccg tttagaggcc ccaagggqtt atgctagtga attctgcagg gtacccgggg
 781 atcctctaga gatccctcga cctcgagatc cattgtgctg gcgcggattc tttatcactg
 841 ataagttggt ggacatacta tgtttatcag tgataaagtg tcaagcatga caaagttgca
 901 gccgaataca gtgatccgtg ccggccctgg actgttgaac gaggtcggcg tagacggtct
 961 gacgacacgc aaactggcgg aacggttggg ggtgcagcag ccggcgcttt actggcactt
1021 caggaacaag cgggcgctgc tcgacgcact ggccgaagcc atgctggcg agaatcatac
1081 gcttcggtgc cgagagccga cgacgactgc gctcatttc tgatcgggaa tcccgcagct
1141 tcaggcaggc gctgctcgcc taccgccagc acaatggatc tcgagggatc ttccatacct
1201 accagttctg cgcctgcagg tgcggccgc gactctctag acgcgtaagc ttactagcat
1261 aaccccttgg ggcctctaaa cgggtcttga ggggttttt gagcttctcg ccctatagtg
1321 agtcgtatta cagcttgagt attctatagt gtcacctaaa tagcttggcg taatcatggt
1381 catagctgtt tcctgtgtga aattgttatc cgctcacaat tccacacaac atacgagccg
1441 gaagcataaa gtgtaaagcc tggggtgcct aatgagtgag ctaactcaca ttaattgcgt
1501 tgcgctcact gcccgctttc cagtcgggaa acctgtcgtg ccagctgcat taatgaatcg
1561 gccaacgcgc ggggagaggc ggtttgcgta ttgggcgctc ttccgcttcc tcgctcactg
1621 actcgctgcg ctcggtcgtt cggctgcggc gagcggtatc agctcactca aaggcggtaa
1681 tacggttatc cacagaatca gggataacg caggaaagaa catgtgagca aaaggccagc
1741 aaaaggccag gaaccgtaaa aaggccgcgt tgctggcgtt tttcgatagg ctccgcccc
1801 ctgacgagca tcacaaaaat cgacgctcaa gtcagaggtg gcgaaacccg acaggactat
1861 aaagatacca ggcgtttccc cctggaagct ccctcgtgcg ctctcctgtt ccgaccctgc
1921 cgcttaccgg atacctgtcc gcctttctcc cttcgggaag cgtggcgctt tctcatagct
1981 cacgctgtag gtatctcagt tcggtgtagg tcgttcgctc caagctgggc tgtgtgcacg
2041 aaccccccgt tcagcccgac cgctgcgcct tatccggtaa ctatcgtctt gagtccaacc
2101 cggtaagaca cgacttatcg ccactggcag cagccactgg taacaggatt agcagagcga
2161 ggtatgtagg cggtgctaca gagtccttga agtggtggcc taactacggc tacactagaa
2221 ggacagtatt tggtatctgc gctctgctga agccagttac cttcggaaaa agagttggta
2281 gctcttgatc cggcaaacaa accaccgctg gtagcggtgg tttttttgtt tgcaagcagc
2341 agattacgcg cagaaaaaaa ggatctcaag aagatccttt gatcttttct acgggqtctg
2401 acgctcagtg gaacgaaaac tcacgttaag ggattttggt catgagatta tcaaaaagga
2461 tcttcaccta gatcctttta aattaaaaat gaagttttaa atcaatctaa agtatatatg
2521 agtaaacttg gtctgacagt taccaatgct taatcagtga ggcacctatc tcagcgatct
2581 gtctatttcg ttcatccata gttgcctgac tccccgtcgt gtagataact acgatacggg
2641 agggcttacc atctggcccc agtgctgcaa tgataccgcg agacccacgc tcaccggctc
2701 cagatttatc agcaataaac cagccagccg aaagggccga gcgcagaagt ggtcctgcaa
2761 ctttatccgc ctccatccag tctattaatt gttgccggga agctagagta agtagttcgc
2821 cagttaatag tttgcgcaac gttgttggca ttgctacagg catcgtggtg tcacgctcgt
2881 cgtttggtat ggcttcattc agctccggtt cccaacgatc aaggcgagtt acatgatccc
2941 ccatgttgtg caaaaaagcg gttagctcct tcggtcctcc gatcgttgtc agaagtaagt
3001 tggccgcagt gttatcactc atggttatgg cagcactgca taattctctt actgtcatgc
3061 catccgtaag atgcttttct gtgactggtg agtactcaac caagtcattc tgagaatacc
3121 gcgccggcg accgagttgc tcttgccggg cgtcaatacg ggataatagt gtatgacata
3181 gcagaacttt aaaagtgctc atcattggaa aacgttcttc gggcgaaaa ctctcaagga
3241 tcttaccgct gttgagatcc agttcgatgt aacccactcg tgcacccaac tgatcttcag
3301 catcttttac tttcaccagc gtttctgggt gagcaaaaac aggaaggcaa aatgccgcaa
3361 aaaagggaat aaggcgaca cggaaatgtt gaatactcat actcttcctt tttcaatatt
3421 attgaagcat ttatcagggt tattgtctca tgagcggata catatttgaa tgtatttaga
3481 aaaataaaca aatagggt ccgcgcacat ttccccgaaa agtgccacct gacgtctaag
3541 aaaccattat tatcatgaca ttaacctata aaaataggcg tatcacgagg ccctttcgtc
3601 tcgcgcgttt cggtgatgac ggtgaaaacc tctgacacat gcagctcccg gagacggtca
3661 cagcttgtct gtaagcggat gccgggagca gacaagcccg tcagggcgcg tcagcgggtg
3721 ttggcgggtg tcgggctgg cttaactatg cggcatcaga gcagattgta ctga
```

FIG. 12.

pGK39

```
TAATACGACT CACTATAGGG CGAATTCAAA AAACCCCTCA AGACCCGTTT
AGAGGCCCCA AGGGGTTATG CTAGTGAATT CTCCAGCCGT ACCCGGGGAT
CCTCTAGAGA TCCCTCGACC TCGAGATCCA TTGTGCTGGA AAGATCACAA
GTTTGTACAA AAAAGCTGAA CGAGAAACGT AAAATGATAT AAATATCAAT
ATATTAAATT AGATTTTGCA TAAAAAACAG ACTACATAAT ACTGTAAAAC
ACAACATATC CAGTCACTAT GGCGGCCGCA TTAGGCACCC CAGGCTTTAC
ACTTTATGCT TCCGCTCGT ATAATGTGTG GATTTTGAGT TAGGATCCGG
CGAGATTTTC AGGAGCTAAG GAAGCTAAAA TGGAGAAAAA AATCACTGGA
TATACCACCG TTGATATATC CCAATGGCAT CGTAAAGAAC ATTTTGAGGC
ATTTCAGTCA GTTGCTCAAT GTACCTATAA CCAGACCGTT CAGCTGGATA
TTACGGCCTT TTTAAAGACC GTAAAGAAAA ATAAGCACAA GTTTTATCCG
GCCTTTATTC ACATTCTTGC CCGCCTGATG AATGCTCATC CGGAATTCCG
TATGGCAATG AAAGACGGTG AGCTGGTGAT ATGGGATAGT GTTCACCCTT
GTTACACCGT TTTCCATGAG CAAACTGAAA CGTTTTCATC GCTCTGGAGT
GAATACCACG ACGATTTCCG GCAGTTTCTA CACATATATT CGCAAGATGT
GGCGTGTTAC GGTGAAAACC TGGCCTATTT CCCTAAAGGG TTTATTGAGA
ATATGTTTTT CGTCTCAGCC AATCCCTGGG TGAGTTTCAC CAGTTTTGAT
TTAAACGTGG CCAATATGGA CAACTTCTTC GCCCCCGTTT TCACCATGGG
CAAATATTAT ACGCAAGGCG ACAAGGTGCT GATGCCGCTG GCGATTCAGG
TTCATCATGC CGTCTGTGAT GGCTTCCATG TCGGCAGAAT GCTTAATGAA
TTACAACAGT ACTGCGATGA GTGGCAGGGC GGCCGTAAA GATCTGGATC
CGGCTTACTA AAAGCCAGAT AACAGTATGC GTATTTGCGC GCTGATTTTT
GCGGTATAAG AATATATACT GATATGTATA CCCGAAGTAT GTCAAAAAGA
GGTGTGCTAT GAAGCAGCGT ATTACAGTGA CAGTTGACAG CGACAGCTAT
CAGTTGCTCA ACGCATATAT GATGTCAATA TCTCCGGTCT GGTAAGCACA
ACCATGCAGA ATGAAGCCCG TCGTCTGCGT GCCGAACGCT GGAAAGCGGA
AAATCAGGAA GGGATGGCTG AGGTCGCCCG GTTTATTGAA ATGAACGGCT
CTTTTGCTGA CGAGAACAGG GACTGGTGAA ATGCAGTTTA AGGTTTACAC
CTATAAAAGA GAGAGCCGTT ATCGTCTGTT TGTGGATGTA CAGAGTGATA
TTATTGACAC GCCCGGGCGA CGGATGGTGA TCCCCCTGGC CAGTGCACGT
CTGCTGTCAG ATAAAGTCTC CCGTGAACTT TACCCGGTGG TGCATATCGG
GGATGAAAGC TGGCGCATGA TGACCACCGA TATGGCCAGT GTGCCGGTCT
CCGTTATCGG GGAAGAAGTG GCTGATCTCA CCCACCGCGA AAATGACATC
AAAAACGCCA TTAACCTGAT GTTCTGGGGA ATATAAATGT CAGGCTCCCT
TATACACAGC CAGTCTGCAG GTCGACCATA GTGACTGGAT ATGTTGTGTT
TTACAGTATT ATGTAGTCTG TTTTTTATGC AAAATCTAAT TTAATATATT
GATATTTATA TCATTTTACG TTTCTCGTTC AGCTTTCTTG TACAAAGTGG
TGATCTTTCC AGCACAATGG ATCTCGAGGG ATCTTCCATA CCTACCAGTT
CTGCGCCTGC AGGTCGCGGC CGCGACTCTA GACGCGTAAG CTTACTAGCA
TAACCCCTTG GGGCCTCTAA ACGCGTCTTC ACGGGTTTTT TGAGCTTCTC
GCCCTATAGT GAGTCGTATT ACAGCTTGAG TATTCTATAG TGTCACCTAA
ATAGCTTGGC GTAATCATGG TCATAGCTGT TTCCTGTGTG AAATTGTTAT
CCGCTCACAA TTCCACACAA CATACGAGCC GGAAGCATAA AGTGTAAAGC
```

FIG. 12 (CONTINUED 1)

```
CTGGGGTGCC TAATGAGTGA GCTAACTCAC ATTAATTGCG TTGCGCTCAC
TGCCCGCTTT CCAGTCGGGA AACCTGTCGT GCCAGCTGCA TTAATGAATC
GGCCAACGCG CGGGGAGAGG CGGTTTGCGT ATTGGGCGCT CTTCCGCTTC
CTCGCTCACT GACTCGCTGC GCTCGGTCGT TCGGCTGCGG CGAGCGGTAT
CAGCTCACTC AAAGGCGGT ATACGGTTAT CCACAGAATC AGGGGATAAC
GCAGGAAAGA ACATGTGAGC AAAAGGCCAG CAAAAGCCCA GGAACCGTAA
AAAGGCCGCG TTGCTGGCGT TTTTCGATAG GCTCCGCCCC CCTGACGAGC
ATCACAAAAA TCGACGCTCA AGTCAGAGGT GGCGAAACCC GACAGGACTA
TAAAGATACC AGGCGTTTCC CCCTGGAAGC TCCCTCGTGC GCTCTCCTGT
TCCGACCCTG CCGCTTACCG GATACCTGTC CGCCTTTCTC CCTTCGGGAA
GCGTGGCGCT TTCTCATAGC TCACGCTGTA GGTATCTCAG TTCGGTGTAG
GTCGTTCGCT CCAAGCTGGG CTGTGTGCAC GAACCCCCCG TTCAGCCCGA
CCGCTGCGCC TTATCCGGTA ACTATCGTCT TGAGTCCAAC CCGGTAAGAC
ACGACTTATC GCCACTGGCA GCAGCCACTG GTAACAGGAT TAGCAGAGCG
AGGTATGTAG GCGGTGCTAC AGAGTTCTTG AAGTGGTGGC CTAACTACGG
CTACACTAGA AGGACAGTAT TTGGTATCTG CGCTCTGCTG AAGCCAGTTA
CCTTCGGAAA AAGAGTTGGT AGCTCTTGAT CCGGCAAACA AACCACCGCT
GGTAGCGGTG GTTTTTTTGT TTGCAAGCAG CAGATTACGC GCAGAAAAAA
AGGATCTCAA GAAGATCCTT TGATCTTTTC TACGGGGTCT GACGCTCAGT
GGAACGAAAA CTCACGTTAA GGGATTTTGG TCATGAGATT ATCAAAAAGG
ATCTTCACCT AGATCCTTTT AAATTAAAAA TGAAGTTTTA AATCAATCTA
AAGTATATAT GAGTAAACTT GGTCTGACAG TTACCAATGC TTAATCAGTG
AGGCACCTAT CTCAGCGATC TGTCTATTTC GTTCATCCAT AGTTGCCTGA
CTCCCCGTCG TGTAGATAAC TACGATACGG GAGGGCTTAC CATCTGCCCC
CAGTGCTGCA ATGATACCGC GAGACCCACG CTCACCGGCT CCAGATTTAT
CAGCAATAAA CCAGCCAGCC GGAAGGGCCG AGCGCAGAAG TGGTCCTGCA
ACTTTATCCG CCTCCATCCA GTCTATTAAT TGTTGCCGGG AAGCTAGAGT
AAGTAGTTCG CCAGTTAATA GTTTGCGCAA CGTTGTTGGC ATTGCTACAG
GCATCGTGGT GTCACGCTCG TCGTTTGGTA TGGCTTCATT CAGCTCCGGT
TCCCAACGAT CAAGGCGAGT TACATGATCC CCCATGTTGT GCAAAAAAGC
GGTTAGCTCC TTCGGTCCTC CGATCGTTGT CAGAAGTAAG TTGGCCGCAG
TGTTATCACT CATGGTTATG GCAGCACTGC ATAATTCTCT TACTGTCATG
CCATCCGTAA GATGCTTTTC TGTGACTGGT GAGTACTCAA CCAAGTCATT
CTGAGAATAC CGCGCCCGGC GACCGAGTTG CTCTTGCCCG GCGTCAATAC
GGGATAATAC TGTATGACAT AGCAGAACTT AAAAGTGCT CATCATTGGA
AAACGTTCTT CGGGGCGAAA ACTCTCAAGG ATCTTACCGC TGTTGAGATC
CAGTTCGATG TAACCCACTC GTGCACCCAA CTGATCTTCA GCATCTTTTA
CTTTCACCAG CGTTTCTGGG TGAGCAAAAA CAGGAAGGCA AAATGCCGCA
AAAAAGGGAA TAAGGGCGAC ACGGAAATGT TGAATACTCA TACTCTTCCT
TTTTCAATAT TATTGAAGCA TTTATCAGGG TTATTGTCTC ATGAGCGGAT
ACATATTTCA ATGTATTTAG AAAAATAAAC AAATAGGGGT TCCGCGCACA
TTTCCCCGAA AAGTGCCACC TGACGTCTAA GAAACCATTA TTATCATGAC
ATTAACCTAT AAAAATAGGC GTATCACGAG GCCCTTTCGT CTCGCGCGTT
TCGGTGATGA CGGTGAAAAC CTCTGACACA TGCAGCTCCC GGAGACGGTC
ACAGCTTGTC TGTAAGCGGA TGCCGGGAGC AGACAAGCCC GTCAGGGCGC
GTCAGCGGGT GTTGGCGGGT GTCGGGCTG GCTTAACTAT GCGGCATCAG
```

FIG. 12 (CONTINUED 2)

```
AGCAGATTGT ACTGAGAGTG CACCATATGC GGTGTGAAAT ACCGCACAGA
TGCGTAAGGA GAAAATACCG CATCAGGCGA AATTGTAAAC GTTAATATTT
TGTTAAAATT CGCGTTAAAT ATTTGTTAAA TCAGCTCATT TTTTAACCAA
TAGGCCGAAA TCGGCAAAAT CCCTTATAAA TCAAAAGAAT AGACCGAGAT
AGGGTTGAGT GTTGTTCCAG TTTGGAACAA GAGTCCACTA TTAAAGAACG
TGGACTCCAA CGTCAAAGGG CGAAAAACCG TCTATCAGGG CGATGGCCCA
CTACGTGAAC CATCACCCAA ATCAAGTTTT TTGCGGTCGA GGTCCCGTAA
AGCTCTAAAT CGGAACCCTA AAGGGAGCCC CCGATTTAGA GCTTGACGGG
GAAAGCCGGC GAACGTGGCG AGAAAGGAAG GGAAGAAAGC GAAAGGAGCG
GGCGCTAGGG CGCTGGCAAG TGTAGCGGTC ACGCTGCGCG TAACCACCAC
ACCCGCCGCG CTTAATGCGC CGCTACAGGG CGCGTCCATT CGCCATTCAG
GCTGCGCAAC TGTTGGGAAG GGCGATCGGT GCGGGCCTCT TCGCTATTAC
GCCAGCTGGC GAAAGGGGGA TGTGCTGCAA GGCGATTAAG TTGGGTAACG
CCAGGGTTTT CCCAGTCACG ACGTTGTAAA ACGACGGCCA GTGAATTG
```

FIG. 13.

TopoRNAi
```
   1 gagtgcacca tatgcggtgt gaaataccgc acagatgcgt aaggagaaaa taccgcatca
  61 ggcgaaattg taaacgttaa tattttgtta aaattcgcgt taaatatttg ttaaatcagc
 121 tcatttttta accaataggc cgaaatcggc aaatccctt ataaatcaaa agaatagacc
 181 gagataggqt tgagtgttgt tccagtttgg aacaagagtc cactattaaa gaacgtggac
 241 tccaacgtca aagggcgaaa aaccgtctat cagggcgatg gcccactacg tgaaccatca
 301 cccaaatcaa gttttttgcg gtcgaggtgc cgtaaagctc taaatcggaa ccctaaaggg
 361 agccccgat ttagagcttg acggggaaag ccggcgaacg tggcgagaaa ggaagggaag
 421 aaagcgaaag gagcggccgc tagggcgctg gcaagtgtag cggtcacgct gcgcgtaacc
 481 accacaccg ccgcgcttaa tgcgccgcta cagggcgcgt ccattcgcca ttcaggctgc
 541 gcaactgttg cgaaggacga tcggtgcggg cctcttcgct attacgccag ctggcgaaag
 601 ggggatgtgc tgcaaggcga ttaagttggg taacgccagg gttttcccag tcacgacgtt
 661 gtaaaacgac ggccagtgaa ttgtaatacg actcactata gggcgaattc aaaaaacccc
 721 tcaagaccc tttagaggcc ccaaggggtt atgctagtga attctgcagg taccggggg
 781 atcctctaga gatccctcga cctcgagatc cattgtggcg gaattctacc aaggctagca
 841 tgggcagccg aatacagtga tccgtgccgg ccctggactg ttgaacgagg tggcgtaga
 901 cggtctgacg acacgcaaac tgccggaacg gttgggggtg cagcagccgg cgctttactg
 961 gcacttcagg aacaagcggg cgctgctcga cgcactggcc gaagccatgc tggcggagaa
1021 tcatacgctt cggtgccgag agccgacgac gactggcgct catttctgat cgggaatccc
1081 gcagccatgc tagccttggt agaattccac cacaatggat ctcgagggat cttccatacc
1141 taccagttct gcgcctgacc gtcgcggccg cgactctcta gacgcgtaag cttactagca
1201 taaccccttg gggcctctaa acgggtcttg agggattttt tgagcttctc gccctatagt
1261 gagtcgtatt acagcttgag tattctatag tgtcacctaa atagcttggc gtaatcatcg
1321 tcatagctgt ttcctgtgtg aaattgttat ccgctcacaa ttccacacaa catacgagcc
1381 ggaagcataa agtgtaaagc ctggggtgcc taatgagtga gctaactcac attaattgcg
1441 ttgcgctcac tgcccgcttt ccagtcggga aacctgtcgt gccagctgca ttaatgaatc
1501 ggccaacgcg cggggagagg cggtttgcgt attgggcgct cttccgcttc ctcgctcact
1561 gactcgctgc gctcggtcgt tcggctgcgg cgagcggtat cagctcactc aaaggcggta
1621 atacggttat ccacagaatc agggggataac gcaggaaaga acatgtgagc aaaaggccag
1681 caaaaggcca ggaaccgtaa aaaggccgcg ttgctggcgt ttttccatag gctccgcccc
1741 cctgacgagc atcacaaaaa tcgacgctca agtcagaggt ggcgaaaccc gacaggacta
1801 taaagatacc aggcgtttcc ccctggaagc tccctcgtgc gctctcctgt tccgaccctg
1861 ccgcttaccg gatacctgtc cgcctttctc ccttcgggaa gcgtggcgct ttctcatagc
1921 tcacgctgta ggtatctcag ttcggtgtag gtcgttcgct ccaagctggg ctgtgtgcac
1981 gaacccccg ttcagcccga ccgctgcgcc ttatccggta actatcgtct tgagtccaac
2041 ccggtaagac acgacttatc gccactggca gcagccactg gtaacaggat tagcagagcg
2101 aggtatgtag gcggtgctac agagttcttg aagtggtggc ctaactacgg ctacactaga
2161 aggacagtat ttggtatctg cgctctgctg aagccagtta ccttcggaaa aagagttggt
2221 agctcttgat ccggcaaaca aaccaccgct ggtagcggtg gtttttttgt ttgcaagcag
2281 cagattacgc gcagaaaaaa aggatctcaa gaagatcctt tgatctttc tacgcggtct
2341 gacgctcagt ggaacgaaaa ctcacgttaa gggattttgg tcatgagatt atcaaaaagg
2401 atcttcacct agatcctttt aaattaaaaa tgaagtttta aatcaatcta agtatatat
2461 gagtaaactt ggtctgacag ttaccaatgc ttaatcagtg aggcacctat ctcagcgatc
2521 tgtctatttc gttcatccat agttgcctga ctccccgtcg tgtagataac tacgatacgg
2581 gagggcttac catctggccc cagtgctgca atgataccgc gagacccacg ctcaccggct
2641 ccagatttat cagcaataaa ccagccagcc ggaagggccg agcgcagaag tggtcctgca
2701 actttatcca cctccatcca gtctattaat tgttgccggg aagctagagt aagtagttcg
2761 ccagttaata gtttgcgcaa cgttgttggc attgctacag gcatcgtggt gtcacgctcg
2821 tcgtttggta tggcttcatt cagctccggt tcccaacgat caaggcgagt tacatgatcc
2881 cccatgttgt gcaaaaaagc ggttagctcc ttcggtcctc cgatcgttgt cagaagtaag
2941 ttggccgcag tgttatcact catggttatg gcagcactgc ataattctct tactgtcatg
3001 ccatccgtaa gatgcttttc tgtgactggt gagtactcaa ccaagtcatt ctgagaatac
3061 cgcgcccgc gaccgagttg ctcttgcccg gcgtcaatac gggataatag tgtatgacat
3121 agcagaactt taaaagtgct catcattgga aaacgttctt cggggcgaaa actctcaagg
3181 atcttaccgc tgttgagatc cagttcgatg taacccactc gtgcacccaa ctgatcttca
3241 gcatctttta ctttcaccag cgtttctggg tgagcaaaaa caggaaggca aaatgccgca
3301 aaaaggggaa taagggcgac acggaaatgt tgaatactca tactcttcct ttttcaatat
3361 tattgaagca tttatcaggg ttattgtctc atgagcggat acatatttga atgtatttag
3421 aaaataaaca aatagggggt tccgcgcaca tttccccgaa aagtgccacc tgacgtctaa
3491 gaaaccatta ttatcatgac attaacctat aaaaatoggo gtatcacgag gccctttcgt
3541 ctcgcgcgtt tcggtgatga cggtgaaaac ctctgacaca tgcagctccc ggagacggtc
3601 acagcttgtc tgtaagcgga tgccgggagc agacaagccc gtcagggcgc gtcagcgggt
3661 gttggcgggt gtcggggctg gcttaactat gcggcatcag agcagattgt actga
```

FIG. 14.

pGN49A

```
TGTAATACGA CTCACTATAG GGCGAATTCA AAAAACCCCT CAAGACCCGT
TTAGAGGCCC CAAGGGGTTA TGCTAGTGAA TTCTGCAGCG GTACCCGGGG
ATCCTCTAGA GATCCCTCGA CCTCGAGATC CATTGTGCTG GAAAGGATCT
GGATCCGGCT TACTAAAAGC CAGATAACAG TATGCCTATT GCGCGCTGA
TTTTTGCGGT ATAAGAATAT ATACTGATAT GTATACCCGA AGTATGTCAA
AAAGAGGTGT GCTATGAAGC AGCGTATTAC AGTGACAGTT GACAGCGACA
GCTATCAGTT GCTCAAGGCA TATATGATGT CAATATCTCC GGTCTGGTAA
GCACAACCAT CCAGAATCAA GCCCGTCGTC TGCGTGCCGA ACGCTGGAAA
GCGGAAAATC AGGAAGGGAT GGCTGAGGTC GCCCGGTTTA TTGAAATGAA
CGGCTCTTTT GCTGACGAGA ACAGGGACTG GTGAAATGCA GTTTAAGGTT
TACACCTATA AAAGAGAGAG CCGTTATCGT CTGTTTGTCC ATGTACAGAG
TGATATTATT GACACGCCCG GGCGACGGAT GGTGATCCCC CTGGCCAGTG
CACGTCTCTT AAGCGATAAA GTCTCCCGTG AACTTTACCC GGTGGTGCAT
ATCGGGGATG AAAGCTGGCG CATGATGACC ACCGATATGG CCAGTGTGCC
GGTCTCCGTT ATCGGGGAAG AAGTGGCTGA TCTCAGCCAC CGCGAAAATG
ACATCAAAAA CGCCATTAAC CTGATGTTCT GGGGAATATA AATGTCAGGC
TCCCTTATAC ACAGCCTTTC AGCACAATG GATCTCGAGG GATCTTCCAT
ACCTACCAGT TCTGCGCCTG CAGGTCGCGG CCGCGACTCT AGACGCGTAA
GCTTACTAGC ATAACCCCTT GGGGCCTCTA AACGGGTCTT GAGGGGTTTT
TTGAGCTTCT CGCCCTATAG TGAGTCGTAT TACAGCTTGA GTATTCTATA
GTGTCACCTA AATAGCTTGG CGTAATCATG GTCATAGCTG TTTCCTGTGT
GAAATTGTTA TCCGCTCACA ATTCCACACA ACATACGAGC CGGAAGCATA
AAGTGTAAAG CCTGGGGTGC CTAATGAGTG AGCTAACTCA CATTAATTGC
GTTGCGCTCA CTGCCCGCTT TCCAGTCGGG AAACCTGTCG TGCCAGCTGC
ATTAATGAAT CGGCCAACGC GCGGGGAGAG GCGGTTTGCG TATTGGGCGC
TCTTCCGCTT CCTCGCTCAC TGACTCGCTG CGCTCGGTCG TTCGGCTGCG
GCGAGCGGTA TCAGCTCACT CAAAGGCGGT AATACGGTTA TCCACAGAAT
CAGGGGATAA CGCAGGAAAG AACATGTGAG CAAAAGGCCA GCAAAAGGCC
AGGAACCGTA AAAAGGCCGC GTTGCTGGCG TTTTTCGATA GGCTCCGCCC
CCCTGACGAG CATCACAAAA ATCGACGCTC AAGTCAGAGG TGGCGAAACC
CGACAGGACT ATAAAGATAC CAGGCGTTTC CCCCTGGAAG CTCCCTCGTG
CGCTCTCCTG TTCCGACCCT GCCGCTTACC GGATACCTGT CCGCCTTTCT
CCCTTCGGGA AGCGTGGCGC TTTCTCATAG CTCACGCTGT AGGTATCTCA
GTTCGGTGTA GGTCGTTCGC TCCAAGCTGG GCTGTGTGCA CGAACCCCCC
GTTCAGCCCG ACCGCTGCGC CTTATCCGGT AACTATCGTC TTGAGTCCAA
CCCGGTAAGA CACGACTTAT CGCCACTGGC AGCAGCCACT GGTAACAGGA
TTAGCAGAGC GAGGTATGTA GGCGGTGCTA CAGAGTTCTT GAAGTGGTGG
CCTAACTACG GCTACACTAG AAGGACAGTA TTTGGTATCT GCGCTCTGCT
GAAGCCAGTT ACCTTCGGAA AAAGAGTTGG TAGCTCTTGA TCCGGCAAAC
AAACCACCGC TGGTAGCGGT GGTTTTTTTG TTTGTAAGCA GCAGATTACG
CGCAGAAAAA AAGGATCTCA AGAAGATCCT TTGATCTTTT CTACGGGGTC
TGACGCTCAG TGGAACGAAA ACTCACGTTA AGGGATTTTG GTCATGAGAT
TATCAAAAAG GATCTTCACC TAGATCCTTT TAAATTAAAA ATGAAGTTTT
```

FIG. 14 (CONTINUED)

```
AAATCAATCT AAAGTATATA TGAGTAAACT TGGTCTGACA GTTACCAATG
CTTAATCAGT GAGGCACCTA TCTCAGCGAT CTGTCTATTT CGTTCATCCA
TAGTTGCCTG ACTCCCCGTC GTGTAGATAA CTACGATACG GGAGGGCTTA
CCATCTGGCC CCAGTGCTGC AATGATACCG CGAGACCCAC GCTCACCGGC
TCCAGATTTA TCAGCAATAA ACCAGCCAGC CGGAAGGGCC GAGCGCAGAA
GTGGTCCTGC AACTTTATCC GCCTCCATCC AGTCTATTAA TTGTTGCCGG
GAAGCTAGAG TAAGTAGTTC GCCAGTTAAT AGTTTGCGCA ACGTTGTTGG
CATTGCTACA GGCATCGTGG TGTCACGCTC GTCGTTTGGT ATGGCTTCAT
TCAGCTCCGG TTCCCAACGA TCAAGGCGAG TTACATGATC CCCCATGTTG
TGCAAAAAAG CGGTTAGCTC CTTCGGTCCT CCCATCGTTG TCAGAAGTAA
GTTGGCCGCA GTGTTATCAC TCATGGTTAT GGCAGCACTG CATAATTCTC
TTACTGTCAT CCCATCCGTA AGATGCTTTT CTGTGACTGG TGAGTACTCA
ACCAAGTCAT TCTGAGAATA CCGCGCCCGG CGACCGAGTT GCTCTTGCCC
GGCGTCAATA CGGGATAATA GTGTATGACA TAGCAGAACT TTAAAAGTGC
TCATCATTGG AAAACGTTCT TCGGGGCGAA AACTCTCAAG GATCTTACCG
CTGTTGAGAT CCAGTTCGAT GTAACCCACT CGTGCACCCA ACTGATCTTC
AGCATCTTTT ACTTCACCA GCGTTTCTGG GTGAGCAAAA ACAGGAAGGC
AAAATGCCGC AAAAAAGGGA ATAAGGGCGA CACGGAAATG TTGAATACTC
ATACTCTTCC TTTTTCAATA TTATTGAAGC ATTTATCAGG GTTATTGTCT
CATGAGCGGA TACATATTTG AATGTATTTA GAAAAATAAA CAAATAGGGG
TTCCGCGCAC ATTTCCCCGA AAAGTGCCAC CTGACGTCTA AGAAACCATT
ATTATCATGA CATTAACCTA TAAAAATAGC CGTATCACGA GGCCCTTTCG
TCTCGCGCGT TTCGGTGATG ACGGTGAAAA CCTCTGACAC ATGCAGCTCC
CGGAGACGGT CACAGCTTGT CTGTAAGCGG ATGCCGGGAG CAGACAAGCC
CGTCAGGGCG CGTCAGCGGG TGTTGGCGGG TGTCGGCGCT GGCTTAACTA
TGCGGCATCA GAGCAGATTG TACTGAGAGT GCACCATATG CGGTGTGAAA
TACCGCACAG ATCCGTAAGG AGAAAATACC GCATCAGGCC AAATTGTAAA
CGTTAATATT TTGTTAAAAT TCGCGTTAAA TATTTGTTAA ATCAGCTCAT
TTTTTAACCA ATAGGCCGAA ATCGGCAAAA TCCCTTATAA ATCAAAAGAA
TAGACCGAGA TAGGGTTGAG TGTTGTTCCA GTTTGGAACA AGAGTCCACT
ATTAAAGAAC GTGGACTCCA ACGTCAAAGG GCGAAAAACC GTCTATCAGG
GCGATGGCCC ACTACGTGAA CCATCACCCA AATCAAGTTT TTTGCGGTCG
AGGTGCCCTA AAGCTCTAAA TCGGAACCCT AAAGGGAGCC CCCGATTTAG
AGCTTGACGG CGAAAGCCGG CGAACGTGCT GAGAAAGGAA GGGAAGAAAG
CGAAAGGAGC GGGCGCTAGG GCGCTGGCAA GTGTAGCGGT CACGCTGCGC
GTAACCACCA CACCCGCCGC GCTTAATGCG CCGCTACAGG GCGCGTCCAT
TCGCCATTCA GGCTGCGCAA CTGTTGGGAA GGGCGATCGG TGCGGGCCTC
TTCGCTATTA CGCCAGCTGG CGAAAGGGGG ATGTGCTGCA AGGCGATTAA
GTTGGGTAAC GCCAGGGTTT TCCCAGTCAC GACGTTGTAA AACGACGGCC
AGTGAAT
``` pGN534 FIG. 15.

```
GAGTGCACCA TATGCGGTGT GAAATACCGC ACAGATGCGT AAGGAGAAAA
TACCGCATCA GGCGAAATTG TAAACGTTAA TATTTTGTTA AAATTCGCGT
TAAATATTTG TTAAATCAGC TCATTTTTTA ACCAATAGGC CGAAATCGGC
AAAATCCCTT ATAAATCAAA AGAATAGACC GAGATAGGGT TGAGTGTTGT
TCCAGTTTGG AACAAGAGTC CACTATTAAA GAACGTGGAC TCCAACGTCA
AAGCGCGAAA AACCGTCTAT CAGGGCGATG GCCCACTACG TGAACCATCA
CCCAAATCAA GTTTTTTGCG GTCGAGGTCC CCTAAAGCTC TAAATCGGAA
CCCTAAAGGG AGCCCCCGAT TTAGAGCTTG ACGGGGAAAG CCGGCGAACG
TGGCGAGAAA GGAAGGGAAG AAAGCGAAAG GAGCGGGCGC TAGGGCGCTG
GCAAGTGTAG CGGTCACGCT GCGCGTAACC ACCACACCCG CCGCGCTTAA
TGCGCCGCTA CAGGGCGCGT CCATTCGCCA TTCAGGCTGC GCAACTGTTG
GGAAGGGCGA TCGGTGCGGG CCTCTTCGCT ATTACGCCAG CTGGCGAAAG
GGGGATGTGC TGCAAGGCGA TTAAGTTGGG TAACGCCAGG GTTTTCCCAG
TCACGACGTT GTAAAACGAC GGCCAGTGAA TTGTAATACG ACTCACTATA
GGGCGAATTC GAGCTCGGTA CCCGGGGATC CTCTAGAGAT CCCTCGACCT
CGAGATCCAT TGTGCTGGAA AGGATCTGGA TCCGGCTTAC TAAAAGCCAG
ATAACAGTAT GCGTATTTGC GCGCTGATTT TTGCGGTATA AGAATATATA
CTGATATGTA TACCCGAAGT ATGTCAAAAA GAGGTGTGCT ATGAAGCAGC
GTATTACAGT GACAGTTGAC AGCGACAGCT ATCAGTTGCT CAAGGCATAT
ATGATGTCAA TATCTCCGGT CTGGTAAGCA CAACCATGCA GAATGAAGCC
CGTCGTCTGC GTGCCGAACG CTGGAAAGCG GAAATCAGG AAGGCATGGC
TGAGGTCGCC CGGTTTATTG AAATGAACGG CTCTTTTGCT GACGAGAACA
GGGACTGGTG AAATGCAGTT TAAGGTTTAC ACCTATAAAA GAGAGAGCCG
TTATCGTCTG TTTGTGGATG TACAGAGTGA TATTATTGAC ACGCCCGGGC
GACGGATGGT GATCCCCCTG GCCAGTGCAC GTCTCTTAAG CGATAAAGTC
TCCCGTGAAC TTTACCCGGT GGTGCATATC GGGGATGAAA GCTGGCGCAT
GATGACCACC GATATGGCCA GTGTGCCGGT CTCGGTTATC GGGGAAGAAC
TGGCTGATCT CAGCCACCGC GAAAATGACA TCAAAAACGC CATTAACCTG
ATGTTCTGGG AATATAAAT GTCAGGCTCC CTTATACACA GCCTTTCCAG
CACAATGGAT CTCGAGGGAT CTTCCATACC TACCAGTTCT GCGCCTGCAG
GTCGCGGCCG CGACTCTCTA GAGTCGAAAG CTTCTCGCCC TATAGTGAGT
CGTATTACAG CTTGAGTATT CTATAGTGTC ACCTAAATAG CTTGGCGTAA
TCATGGTCAT AGCTGTTTCC TGTGTGAAAT TGTTATCCGC TCACAATTCC
ACACAACATA CGAGCCGGAA GCATAAAGTG TAAAGCCTGG GGTGCCTAAT
GAGTGAGCTA ACTCACATTA ATTGCGTTGC GCTCACTGCC CGCTTTCCAG
TCGGGAAACC TGTCGTGCCA GCTGCATTAA TGAATCGGCC AACGCGCGGG
GAGAGGCGGT TTGCGTATTG GGCGCTCTTC CGCTTCCTCG CTCACTGACT
CGCTGCGCTC GGTCGTTCGG CTGCGGCGAG CGGTATCAGC TCACTCAAAG
GCGGTAATAC GGTTATCCAC AGAATCAGGG GATAACGCAG GAAAGAACAT
GTGAGCAAAA GGCCAGCAAA AGGCCAGGAA CCGTAAAAAG GCCGCGTTGC
TGGCGTTTTT CGATAGGCTC CGCCCCCTG ACGAGCATCA CAAAAATCGA
CGCTCAAGTC AGAGGTGGCG AAACCCGACA GGACTATAAA GATACCAGGC
GTTTCCCCCT GGAAGCTCCC TCGTGCGCTC TCCTGTTCCG ACCCTGCCGC
TTACCGGATA CCTGTCCGCC TTTCTCCCTT CGGGAAGCGT GGCGCTTTCT
```

FIG. 15 (CONTINUED)

```
CATAGCTCAC GCTGTAGGTA TCTCAGTTCG GTGTAGGTCC TTCGCTCCAA
GCTGGGCTGT GTGCACGAAC CCCCCGTTCA GCCCGACCGC TGCGCCTTAT
CCGGTAACTA TCGTCTTGAG TCCAACCCGG TAAGACACGA CTTATCGCCA
CTGGCAGCAG CCACTGGTAA CAGGATTAGC AGAGCGAGGT ATGTAGGCGG
TGCTACAGAG TTCTTGAAGT GGTGGCCTAA CTACGGCTAC ACTAGAAGGA
CAGTATTTGG TATCTGCGCT CTGCTGAAGC CAGTTACCTT CGGAAAAAGA
GTTGGTAGCT CTTGATCCGG CAAACAAACC ACCGCTGGTA GCGGTGGTTT
TTTTGTTTGC AAGCAGCAGA TTACGCGCAG AAAAAAGGA TCTCAAGAAG
ATCCTTTGAT CTTTTCTACG GGGTCTGACG CTCAGTGGAA CGAAAACTCA
CGTTAAGGGA TTTTGGTCAT GAGATTATCA AAAAGGATCT TCACCTAGAT
CCTTTTAAAT TAAAAATGAA GTTTTAAATC AATCTAAAGT ATATATGAGT
AAACTTGGTC TGACAGTTAC CAATGCTTAA TCAGTGAGGC ACCTATCTCA
GCGATCTGTC TATTTCGTTC ATCCATAGTT GCCTGACTCC CCGTCGTGTA
GATAACTACG ATACGGGAGG GCTTACCATC TGGCCCCAGT GCTGCAATGA
TACCGCGAGA CCCACGCTCA CCGGCTCCAG ATTTATCAGC AATAAACCAG
CCAGCCGGAA GGGCCGAGCG CAGAAGTGGT CCTGCAACTT TATCCGCCTC
CATCCAGTCT ATTAATTGTT GCCGGGAAGC TAGAGTAAGT AGTTCGCCAG
TTAATAGTTT GCGCAACGTT GTTGGCATTG CTACAGGCAT CGTCGTGTCA
CGCTCGTCGT TTGGTATGGC TTCATTCAGC TCCGGTTCCC AACGATCAAG
GCGAGTTACA TGATCCCCCA TGTTGTGCAA AAAAGCGGTT AGCTCCTTCG
GTCCTCCGAT CGTTGTCAGA AGTAAGTTGG CCGCAGTGTT ATCACTCATG
GTTATGGCAG CACTGCATAA TTCTCTTACT GTCATGCCAT CCGTAAGATG
CTTTTCTGTG ACTGGTGAGT ACTCAACCAA GTCATTCTGA GAATACCGCG
CCCGGCGACC GAGTTGCTCT TGCCCGGCGT CAATACGGGA TAATAGTGTA
TGACATAGCA GAACTTTAAA AGTGCTCATC ATTGGAAAAC GTTCTTCGGG
GCGAAAACTC TCAAGGATCT TACCGCTGTT GAGATCCAGT TCGATGTAAC
CCACTCGTGC ACCCAACTGA TCTTCAGCAT CTTTTACTTT CACCAGCGTT
TCTGGGTGAG CAAAAACAGG AAGGCAAAAT GCCGCAAAAA AGGGAATAAG
GGCGACACGG AAATGTTGAA TACTCATACT CTTCCTTTTT CAATATTATT
GAAGCATTTA TCAGGGTTAT TGTCTCATGA GCGGATACAT ATTTGAATGT
ATTTAGAAAA ATAAACAAAT AGGGGTTCCG CGCACATTTC CCCGAAAAGT
GCCACCTGAC GTCTAAGAAA CCATTATTAT CATGACATTA ACCTATAAAA
ATAGGCGTAT CACGAGGCCC TTTCGTCTCG CGCGTTTCGG TGATGACGGT
GAAAACCTCT GACACATGCA GCTCCCGGAG ACGGTCACAG CTTGTCTGTA
AGCGGATGCC GGGAGCAGAC AAGCCCGTCA GGGCGCGTCA GCGGGTGTTG
GCGGGTGTCG GGGCTGGCTT AACTATGCGG CATCAGAGCA GATTGTACTG
A
```

VECTOR CONSTRUCTS

RELATED APPLICATIONS

This application claims the benefit under 35 U.S.C. 119 of Great Britain application number GB 0012233.3, filed May 19, 2000.

FIELD OF THE INVENTION

The invention relates to improved vector constructs for use in the expression of double-stranded RNA, particularly for use in the expression of double-stranded RNA in vitro and in vivo.

BACKGROUND OF THE INVENTION

Since the advent of double-stranded RNA inhibition (RNAi) as a tool for controlling gene expression, as described in WO 99/32619 and WO 00/01846, there has been recognized a need for specialized vectors designed for the production of double-stranded RNA (dsRNA).

Cloning vectors designed to produce high levels of dsRNA have been previously described by Plaetinck et al. (WO 00/01846) and Timmons et al. Nature, 395:854 (1998). These vectors generally contain a multiple cloning site (MCS) into which target DNA fragments can be cloned flanked by two opposable transcriptional promoters. Essentially, these three components (Promoter 1, MCS and Promoter 2) make up the entire system. In the appropriate expression system, the DNA cloned into the MCS may be transcribed in both directions, leading to the production of two complementary RNA strands.

A disadvantage of the known systems is that not only the cloned fragment is transcribed. Read-through of the RNA polymerase will result in transcription of the entire vector, and this also in both directions. As only transcription of the cloned DNA fragment will result in active dsRNA for RNAi purposes, transcription of the vector part results in useless, inefficient RNA. More specifically, 80% of these transcripts can be considered as non-specific and thus non-effective.

The large amounts of non-specific RNA generated by the prior art plasmid and expression systems results in some undesirable side effects. First, in RNAi protocols based on introduction of dsRNA into *C. elegans* via a food organism such as *E. coli* which expresses the dsRNA (see WO 00/01846), large RNA strands are considered to be toxic for the food organism. As a result, high amounts of RNA accumulating in *E. coli* cause a significant part of the population to die.

Second, and probably more important, is the reduction of inhibition potential. The presence of large amounts of non-specific dsRNA causes a competitive environment for the specified sequences. The potential of the template-specified dsRNA sequences to inhibit the targeted protein expression in, for instance, *C. elegans* cells is reduced by the presence of these large non-specific regions. Such an inhibition by non-specific dsRNA has also been shown in *Drosophila* by Tushl et al., Genes & Development 13:3191-3197 (1999). Not only the potential to inhibit gene expression is affected, but also the amount of specific dsRNA produced is limited.

Third, transcription of the vector backbone part, more particularly transcription of the origin of replication and related structures, results in plasmid instability and plasmid reorganisation, leading to reduced production of dsRNA. This relatively low concentration of effective dsRNA in turn leads to inefficient RNAi.

To conclude, the previously described vectors have following shortcomings: they are toxic to the feeding organism, a greater proportion of the transcripts produced are non-specific, the inhibitory potential of the dsRNA is reduced by the presence of non-specific regions, a high incidence of plasmid reorganizations and loss of plasmid from the feeding organism. It is therefore an object of the present invention to provide improved vectors for the production of dsRNA which avoid the disadvantages of the prior art vectors.

Vectors for use in the in vitro synthesis of RNA transcripts, for example the production of RNA probes, have been known and commonly used in the art for some time (see for example F. M. Ausubel et al. (eds.), *Current Protocols in Molecular Biology*, John Wiley & Sons, Inc. (1994); Jendrisak et al, Vectors for in vitro production of RNA copies of either strand of a cloned DNA sequence, U.S. Pat. No. 4,766,072). In standard in vitro transcription protocols the problem of read-through transcription of vector sequences is generally avoided by linearizing the transcription vector at restriction site positioned at the 3' end of the desired transcript. However, this solution is not appropriate for in vivo transcription or for the production of dsRNA where it is important that the template is transcribed in both directions.

SUMMARY OF THE INVENTION

The inventors now propose a novel solution to the problems encountered with the prior art vectors for the production of dsRNA, based on the use of transcription terminators. Generally the solution consists of the use of at least one transcription terminator operably linked to at least one promoter, wherein the terminator stops the transcription initiated by the promoter. Any DNA fragment inserted between the 3' end of the promoter and the 5' end of the terminator will then be transcribed, without the unwanted transcription of the vector backbone. Preferentially the vector consists of two promoters and two terminators, as further described below.

Therefore, in accordance with a first aspect of the invention there is provided a DNA construct comprising two opposable promoters flanking an inter-promoter region, the construct further comprising at least one transcription terminator positioned transcriptionally downstream of one of the said promoters. In particular, the invention provides for: a DNA construct comprising:

a) a first promoter and b) a second promoter, in which the first and second promoter are in opposite orientation to each other and define:

c) an inter-promoter region positioned downstream of the 3' end of the first promoter and downstream of the 3' end of the second promoter; and which DNA construct further comprises:

d) at least one cloning site positioned in the inter-promoter region; and e) a first transcription terminator, positioned (as seen from the 3' end of the first promoter) downstream of the first promoter and downstream of the at least one cloning site, wherein the first transcription terminator is operably linked to the first promoter.

The inter-promoter region can also further be defined as: the DNA region between the 3' end of the first promoter and the 3' end of the second promoter, and which is downstream of the first promoter, and which is downstream of the second promoter, and which preferably does not contains the 5' end of the first promoter and of the second promoter. The opposable first promoter and second promoter drive expression directional from their 5' ends to their 3' ends starting transcription downstream of their 3' ends, thus providing transcription of both strands of any nucleotide sequence(s) present in the inter-promoter region.

The two promoters present in the DNA construct of the invention may be identical or they may be different and may be of essentially any type. The precise nature of the promoters used in the construct may be dependent on the nature of the expression system in which the construct is expected to function (e.g. prokaryotic vs eukaryotic host cell). Bacteriophage promoters, for example the T7, T3 and SP6 promoters, are preferred for use in the constructs of the invention, since they provide advantages of high level transcription which is dependent only on binding of the appropriate RNA polymerase. Each of these promoters can independently be chosen. The phage promoters can also function in a wide variety of host systems, i.e. both prokaryotic and eukaryotic hosts, provided that the cognate polymerase is present in the host cell.

The arrangement of two "opposable" promoters flanking an inter-promoter region such that transcription initiation driven by one of the promoters results in transcription of the sense strand of the inter-promoter region and transcription initiation driven by the other promoter results in transcription of the antisense strand of the inter-promoter region is an arrangement well known in the art, for example, in the pGEM7 series of vectors from Promega Corp., Madison Wis., USA.

The DNA constructs of the invention differ from those of the prior art because of the presence of at least one transcription terminator positioned transcriptionally downstream of one of the promoters. The transcription terminator may be uni- or bi-directional, the choice of uni- vs bi-directional terminators being influenced by the positioning of the terminator(s) within or outside the inter-promoter region, as explained below. The terminator may be of prokaryotic, eukaryotic or phage origin. Bacteriophage terminators, for example T7, T3 and SP6 terminators, are particularly preferred. The only requirement is that the terminator must be capable of causing termination of transcription initiating at the promoter relative to which it is transcriptionally downstream. In practice, these means that the promoter and terminator must form a 'functional combination', i.e. the terminator must be functional for the type of RNA polymerase initiating at the promoter. By way of example, a eukaryotic RNA pol II promoter and a eukaryotic RNA pol II terminator would generally form a functional combination. The selection of a functional combination is particularly important where bacteriophage promoters and terminators are to be used in the constructs of the invention, since the phage promoters and terminators are both polymerase-specific. To form a functional combination both the promoter and the terminator should be specific for the same polymerase, e.g. T7 promoter and T7 terminator, T3 promoter and T3 terminator etc.

In one embodiment, the DNA construct of the invention may comprise a single transcription terminator, positioned (as seen from the 3' end of the first promoter) downstream of the first promoter and downstream of the at least one cloning site, wherein the first transcription terminator is operably linked to the first promoter, wherein the single transcription terminator is positioned in the inter-promoter region.

In an alternative arrangement, the DNA construct comprises a single transcription terminator positioned outside of the inter-promoter region. In a still further embodiment, the DNA construct may comprise two transcription terminators, each one of which is positioned transcriptionally downstream of one of the two promoters. In this arrangement, one or both of the terminators may be positioned within the inter-promoter region. These various embodiments of the DNA constructs of the invention will be more fully described below, with reference to the accompanying drawings. The position of a first transcription terminator outside the inter-promoter region may also be further defined as, i.e. such that a first transcription terminator is positioned (as seen from the 3' end of the first promoter) downstream of the first promoter, downstream of the at least one cloning site, and downstream of the 5' end of the second promoter.

The position of a second transcription terminator outside the inter-promoter region may also be further defined as, i.e. such that a second transcription terminator positioned (as seen from the 3' end of the second promoter) downstream of the second promoter, downstream of the at least one cloning site, and downstream of the 5' end of the first promoter.

Moreover, when the terminator is not located in the inter-promoter region, the distance between the 5' end of the first promoter and 3' end of the second terminator, or the distance between the 5' end of the second promoter and the 3' end of the first terminator is preferably small, i.e. such that the 3' end of the first transcription terminator is separated from the 5' end of the second promoter by no more than 2000 nucleotides, preferably no more than 1000 nucleotides, more preferably no more than 500 nucleotides, even more preferably no more than 200 nucleotides, especially preferably no more than 100 nucleotides, more especially preferable no more than 50 nucleotides, even more especially preferably no more than 20 nucleotides, particularly preferably no more than 10 nucleotides, more particularly preferably no more than 6 nucleotides.

Furthermore, when the second transcription terminator is located outside of the inter-promoter region, preferably the 3' end of the second transcription terminator is separated from the 5' end of the first promoter by no more than 2000 nucleotides, preferably no more than 1000 nucleotides, more preferably no more than 500 nucleotides, even more preferably no more than 200 nucleotides, especially preferably no more than 100 nucleotides, more especially preferably no more than 50 nucleotides, even more especially preferably no more than 20 nucleotides, particularly preferably no more than 10 nucleotides, more particularly preferably no more than 6 nucleotides.

As defined above the term 'inter-promoter region' refers to all of the DNA sequence between the two promoters. As explained above, in certain embodiments of the invention the transcription terminator(s) may be sited within the inter-promoter region. The inter-promoter region may, advantageously, comprise a sequence of nucleotides forming a template for dsRNA production. The precise length and nature of this sequence is not material to the invention. The invention further provides DNA constructs in which the inter-promoter region comprises a cloning site. The function of the cloning site is to facilitate insertion of a DNA fragment forming a template for dsRNA production between the two promoters. Thus, the invention provides a series of cloning vectors which are of general use in the construction of template vectors for dsRNA production. Also encompassed within the scope of the invention are vectors derived from the cloning vectors which have a DNA fragment inserted into the cloning site.

The cloning site may further comprise one or more of the following:
  at least one restriction site,(as known in the art), or one or more further restriction sites, e.g. to provide a multiple cloning site(as known in the art),
  a stuffer DNA, e.g., flanked by at least two restriction site, such as two BstXI restriction sites, or two XcmI restriction sites,
  attR1 and attR2 recombination sites,
  a ccdB nucleotide sequence,
  a ccdB nucleotide further comprising at least one unique blunt-end restriction site, such as a SrfI restriction site, and/or a DNA fragment inserted in the at least one cloning site.

All of the DNA constructs provided by the invention may, advantageously, form part of a replicable cloning vector, such as, for example, a plasmid vector. In addition to the opposable promoters, inter-promoter region and transcription terminator(s), the vector 'backbone' may further contain one or more of the general features commonly found in replicable vectors, for example an origin of replication to allow autonomous replication within a host cell and a selective marker, such as an antibiotic resistance gene. The selective marker gene (e.g. the antibiotic resistance gene) may itself contain a promoter and a transcription terminator and it is to be understood that these are completely independent of the promoter and terminator elements required by the invention and are not to be taken into consideration in determining whether a particular vector falls within the scope of the invention.

DNA constructs according to the invention may be easily be constructed from the component sequence elements using standard recombinant techniques well known in the art and described, for example, in F. M. Ausubel et al. (eds.), *Current Protocols in Molecular Biology*, John Wiley & Sons, Inc. (1994), as will be appreciated by one skilled in the art from the following detailed description of the invention and the accompanying Examples.

There follows a detailed description of DNA constructs according to the invention, with reference to the following drawings.

BRIEF DESCRIPTION OF THE DRAWINGS

FIG. 2(a) is a schematic representation of a prior art vector included for comparison purposes.

FIGS. 2(b) to 2(f) are schematic representations of several further embodiments of the DNA construct according to the invention illustrating the use of different cloning sites in the inter-promoter region.

FIG. 9(a) is a representation (plasmid map) of pGN29; FIG. 9(b) is a representation (plasmid map) of pGN39; FIG. 9(c) is a representation (plasmid map) of the plasmid TopoRNAi.

FIG. 10 shows the complete nucleotide sequence of plasmid pGN9 (SEQ ID NO:8).

FIG. 11 shows the complete nucleotide sequence of plasmid pGN29 (SEQ ID NO:9).

FIG. 12 shows the complete nucleotide sequence of plasmid pGN39 (SEQ ID NO:10).

FIG. 13 shows the complete nucleotide sequence of plasmid TopoRNAi (SEQ ID NO:11).

FIG. 14 shows the complete sequence of plasmid pGN49A (SEQ ID NO:12).

FIG. 15 shows the complete sequence of plasmid pGN59A (SEQ ID NO:13).

DETAILED DESCRIPTION OF THE INVENTION

Figure 1:
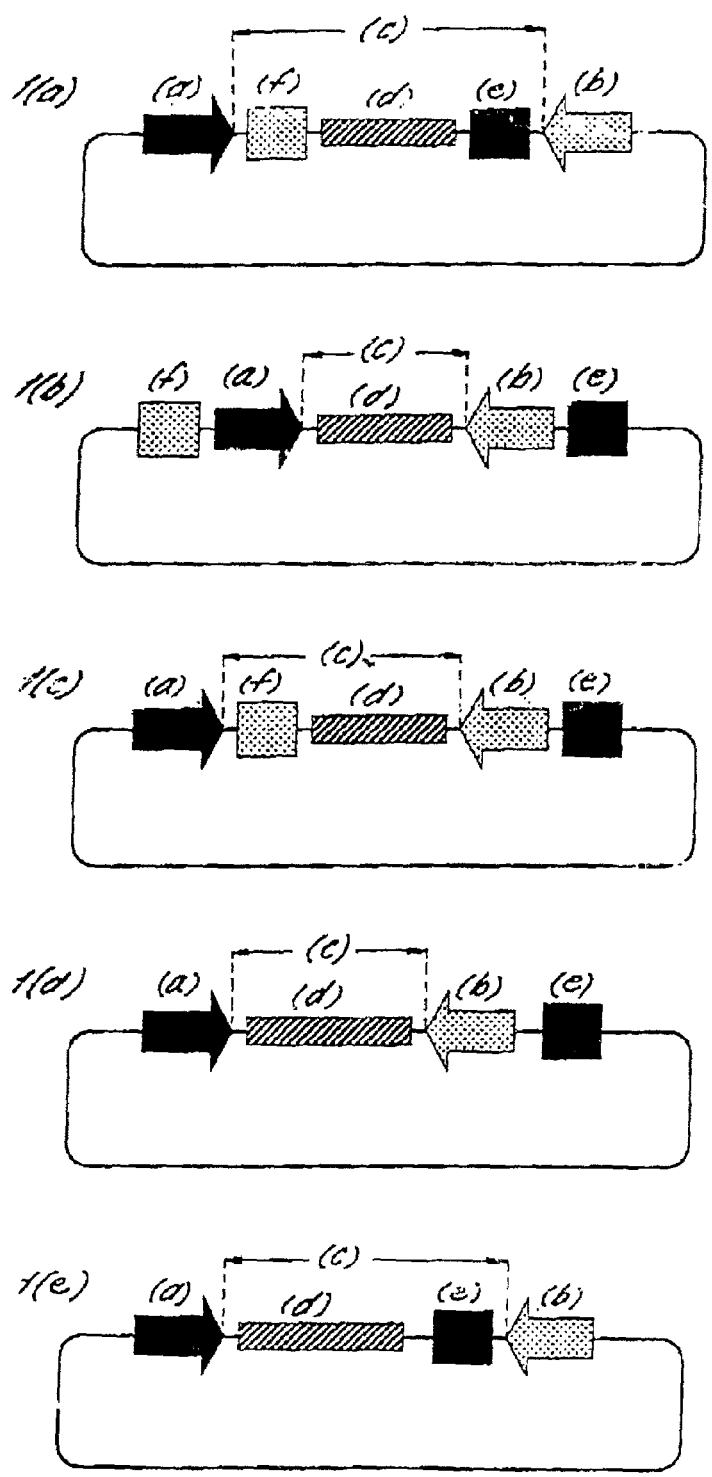
FIGS. 1(a) to 1(e) are schematic representations of several different embodiments of the DNA construct according to the invention illustrating the relative positioning of the promoter and transcription terminator elements.
Figure 3:
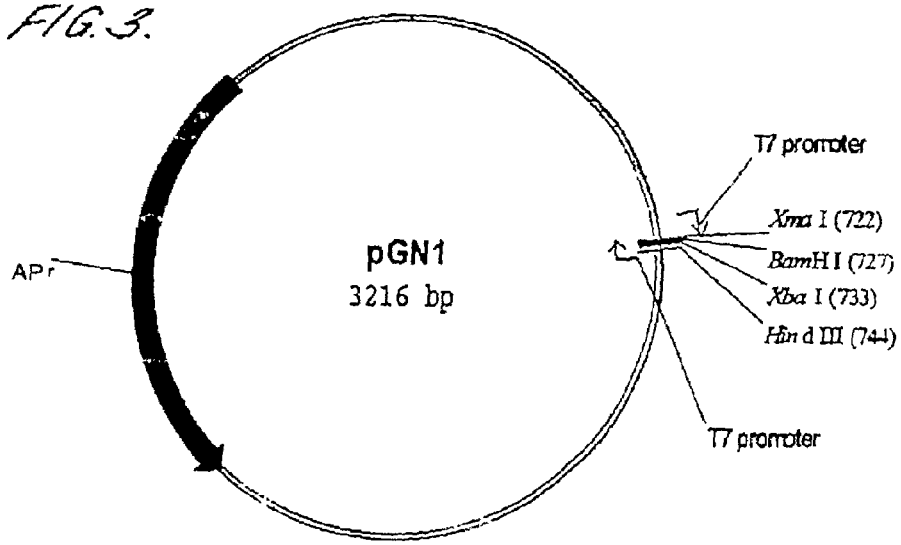
FIG. 3 is a representation (plasmid map) of pGN1.
Figure 4:
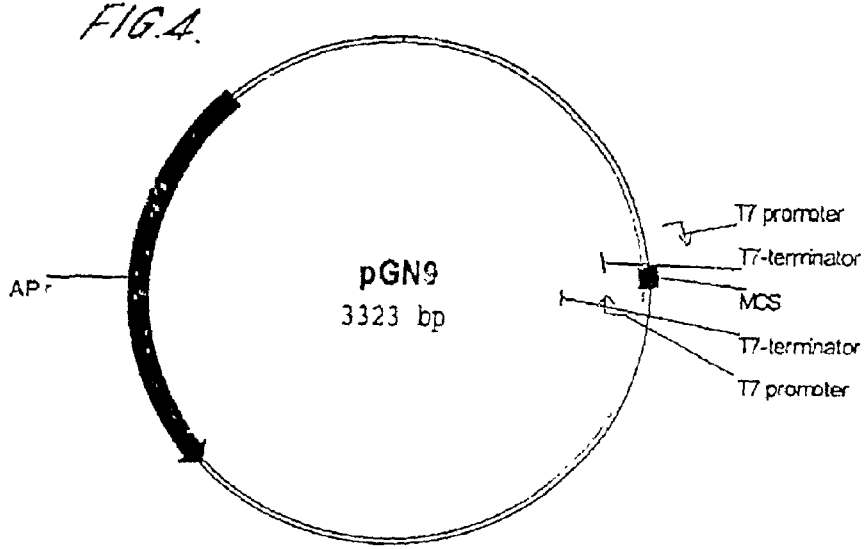
FIG. 4 is a representation (plasmid map) of pGN9.
Figure 5:
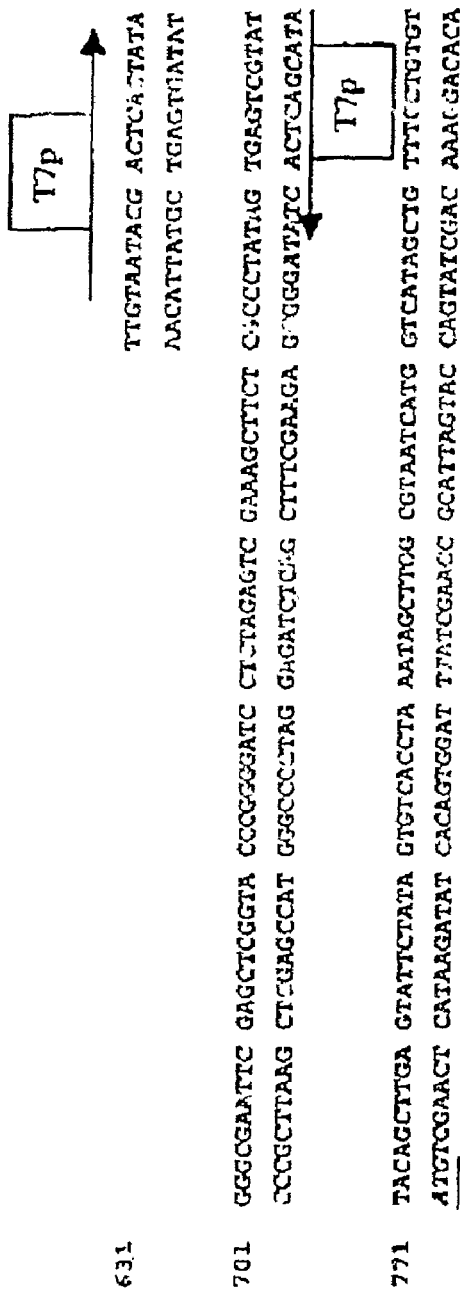
FIG. 5 illustrates the nucleotide sequence of a fragment of plasmid pGN1 (SEQ ID NO:1), annotated to show the positions of the opposable T7 promoters.
Figure 6:
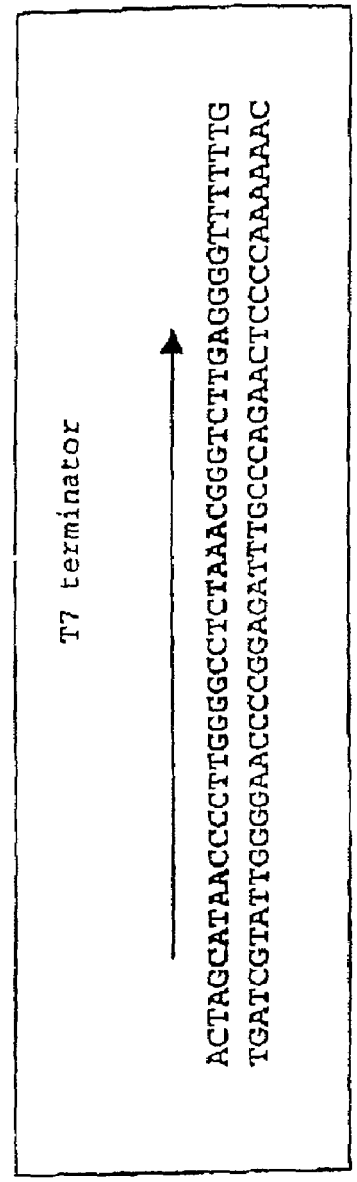
FIG. 6 depicts the nucleotide sequence of the T7 transcription terminator (SEQ ID NO:2).
Figure 7:
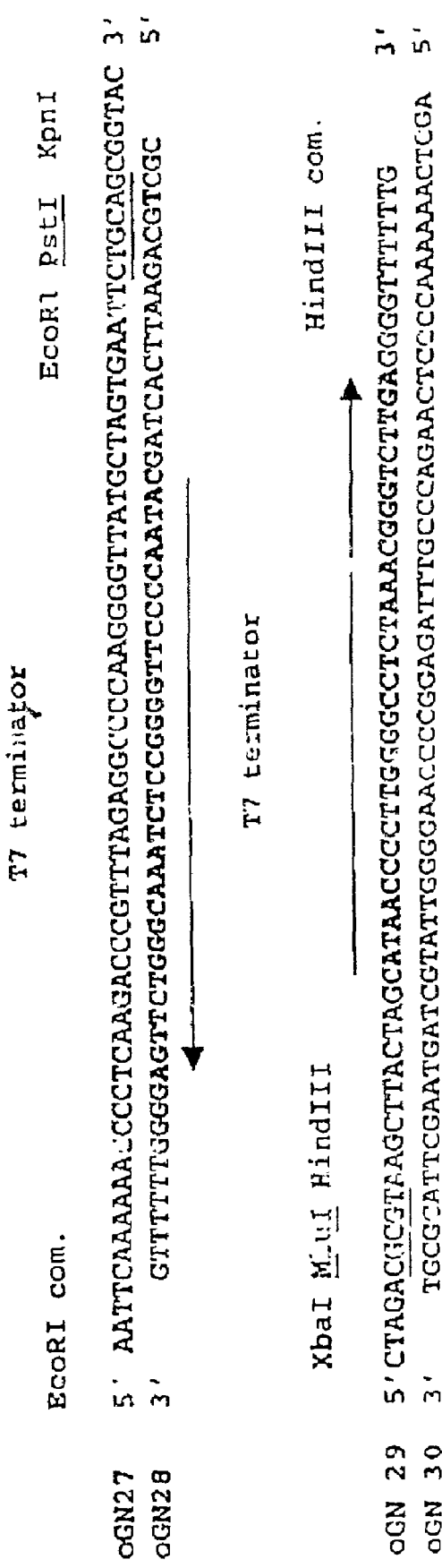
FIG. 7 illustrates the sequences of oligonucleotides oGN27 (SEQ ID NO:3), oGN28 (SEQ ID NO:4), oGN29 (SEQ ID NO:5) and oGN30 (SEQ ID NO:6) used to insert T7 transcription terminators into pGN1. The positions of the T7 pol terminator sequences and of various restriction sites are marked.
Figure 8:
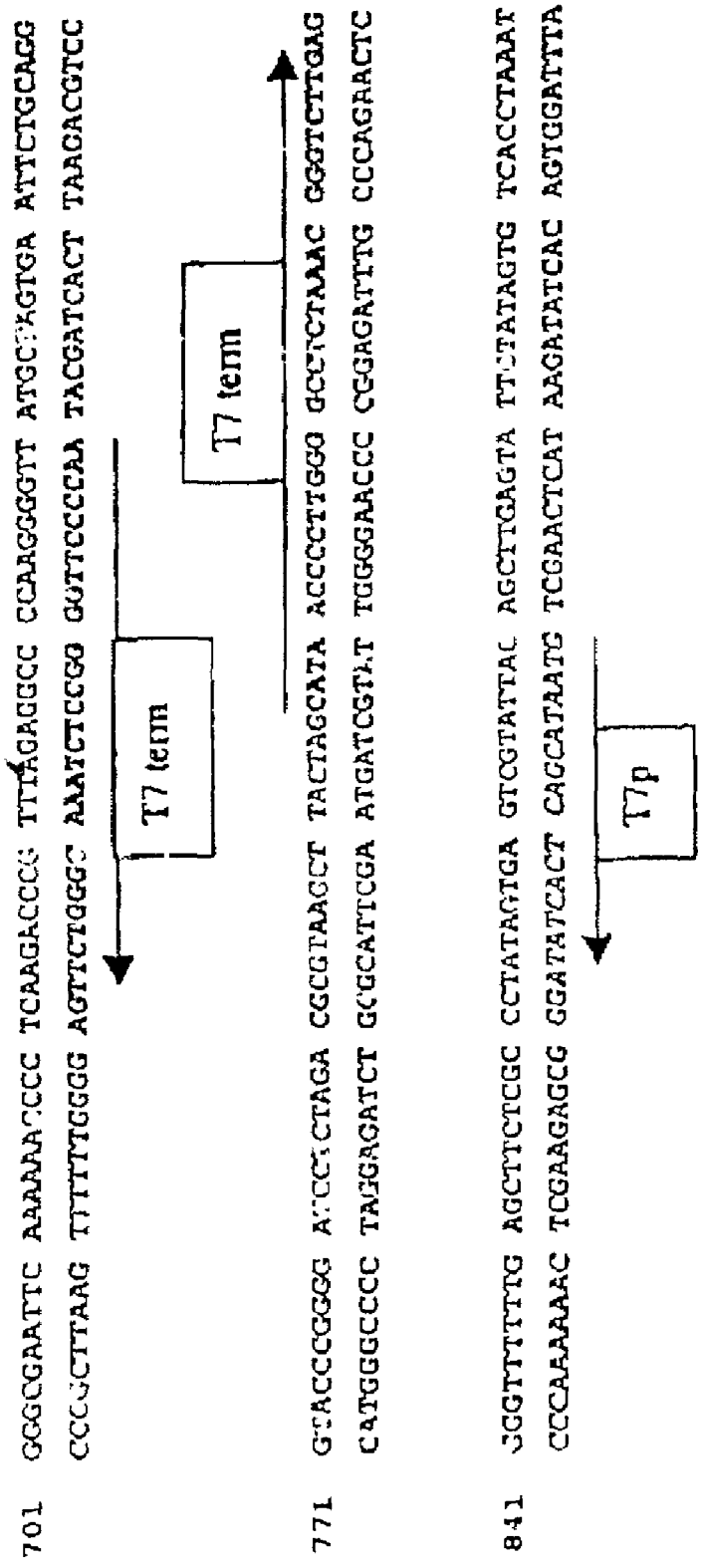
FIG. 8 illustrates the nucleotide sequence of a fragment of plasmid pGN9 (SEQ ID NO:7), annotated to show the positions of the opposable T7 promoters (T7p) and the T7 transcription terminators (T7 term).
Figure 16:
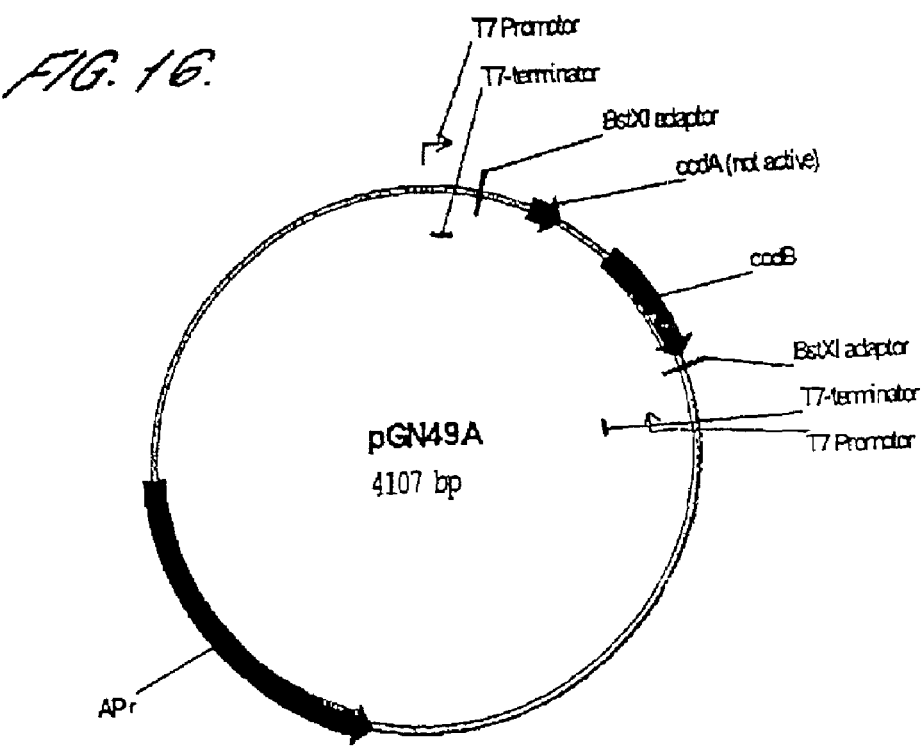
FIG. 16 is a representation (plasmid map) of pGN49A.
Figure 17:
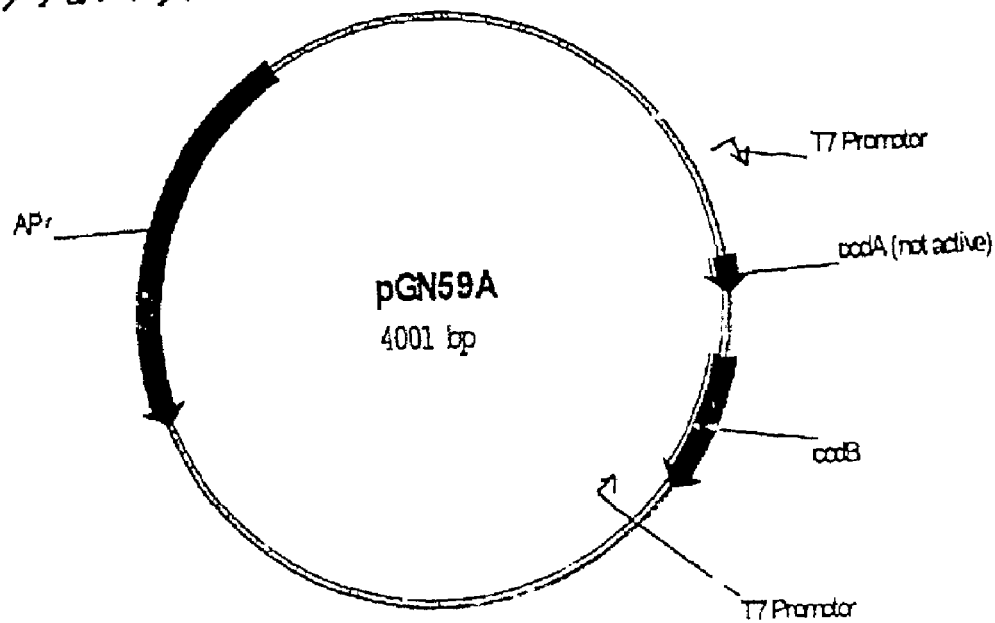
FIG. 17 is a representation (plasmid map) of pGN59A.

Referring to the Drawings, FIG. 1(a) schematically illustrates a first DNA construct according to the invention which is a plasmid vector comprising two opposable promoters; a first promoter (a) and a second promoter (b) flanking an inter-promoter region (c), which inter-promoter region is downstream of the 3' of the first promoter, and down stream of the 3' end of the second promoter. The first promoter and the second promoter may be identical or different. This embodiment comprises a first transcription terminator (e) and a second transcription terminator (f), both of which are positioned within the inter-promoter region. In this embodiment, the first terminator and the second terminator are preferentially uni-directional terminators.

A DNA fragment may be inserted in the at least one cloning site (d). Such DNA fragment is subject to transcription directed by the first promoter (a) and the second promoter (b) (i.e. transcription of both strands), resulting in the generation of two RNA fragments which may combine to form double-stranded RNA of the inserted DNA fragment (both in vitro and in vivo).

Any desired DNA sequence, such as a genomic DNA sequence, or a cDNA sequence or any other coding sequence, may be inserted in the at least one cloning site. Without being limited to any specific explanation, it is assumed that when (a) and (e) form a functional combination, RNA polymerase which initiates transcription at (a) will transcribe the inter-promoter region including the at least cloning site and the DNA fragment inserted in the at least cloning site and will be terminated when it reaches (e). Similarly, RNA polymerase which initiates transcription at (b) will transcribe the inter-promoter region including the at least one cloning site and the DNA fragment inserted in the at least one cloning site and will terminate when it reaches (f). The terminators cause the RNA polymerase to pause, stop transcription and fall off the template. This prevents the unlimited transcription of the vector backbone, and reduces the unspecific transcription of non-essential DNA.

The inter-promoter region further comprises a sequence of nucleotides corresponding to a target for double-stranded RNA inhibition. This sequence is designated 'TF'=for target fragment. It is this sequence which, when transcribed into dsRNA, will be responsible for specific double-stranded RNA inhibition of a target gene. The target fragment may be formed from a fragment of genomic DNA or cDNA from the target gene. Its precise length and nucleotide sequence are not material to the invention.

In the arrangement shown in FIG. 1(a) the two terminators are positioned on either side of the TF within the inter-promoter region. Each of the terminators is positioned transcriptionally downstream of one of the promoters, the fist terminator (e) is transcriptionally downstream of first promoter (a) and the second terminator (f) is transcriptionally downstream of the second promoter (b). Assuming that (a) and (e) form a functional combination, as described above, RNA polymerase which initiates transcription at a) will transcribe the inter-promoter region up to and including TF and will be terminated when it reaches (e). Similarly, RNA polymerase which initiates transcription at (b) will transcribe the inter-promoter region up to and including TF on the opposite strand and will terminate when it reaches (f).

The terminators cause the RNA polymerase to pause, stop transcription and fall off the template. This prevents the unlimited transcription of the vector backbone, and reduces the unspecific transcription of non-essential DNA.

The transcripts generated from this vector may, depending on the precise placement of the terminators in the vector, be almost completely specific dsRNAs corresponding to the TF region. Through the direct placement of the terminator sequences at the downstream end of the TF region on both sides of the inserted DNA fragment, the amount of material transcribed is completely reduced to the template-specified sequences. Therefore, a higher amount of specific dsRNA is obtained. Furthermore the constructs are now also more stable, due to the non-transcription of the vector backbone. The latter characteristic (stability), combined with the now relatively higher specific transcription rate, provides a system adapted to synthesize higher amounts of specific short dsRNA strands. This proportionally higher amount of transcript, resulting in high concentrations of specific dsRNA, enhances the inhibitory effect in RNAi protocols. In RNAi protocols based on expression of dsRNA in a food organism, toxicity for the feeding organisms due to high RNA expression is brought to a minimal level by use of this vector.

A specific example of a vector of the type illustrated in FIG. 1(a), considered by the inventors to be the optimal arrangement for RNAi applications, is plasmid pGN9 described in the accompanying Examples. The transcriptional terminators used in pGN9 are T7 RNA polymerase specific terminators, since the vector contains two opposable T7 promoters. However, other systems could be used such as an expression system based on the T3 or SP6 promoter, terminator and polymerase or other prokaryotic or eukaryotic promoters and terminators.

FIG. 1(b) illustrates schematically a further DNA construct according to the invention which is a plasmid vector comprising two opposable promoters (a) and (b) flanking an inter-promoter region (c). This vector also comprises two transcription terminators (e) and (f) but in this arrangement the two terminators are positioned outside of the inter-promoter region, in fact the terminator elements now flank the two promoters. The arrangement is such that (e) is transcriptionally downstream of (a) whilst (f) is transcriptionally downstream of (b). Here again (e) terminates the transcription initiated by (a), whilst (f) terminates the transcription initiated by promoter (b). Placement of the terminators outside of (d) allows the use of bi-directional terminators as well as uni-directional terminators, in contrast to the arrangement in FIG. 1(a) where uni-directional terminators are preferred because of the placement of the terminators between the promoters. A number of bi-directional terminators which could be used in accordance with the invention are known in the art. Generally these are observed to be polymerase non-specific.

The embodiment shown in FIG. 1(b) provides essentially the same advantages as that shown in FIG. 1(a) over the prior art vectors for dsRNA production. The vector shown in FIG. 1(b) will lead to the production of transcripts which are slightly longer, including the promoter regions. This relatively small difference in the length of the transcript and hence the formed dsRNA will not severely affect the efficacy in an RNAi system.

The position of the terminators and promoter in the example as shown in FIG. 1(b) are preferably placed at close proximity, such that the 5' end of the promoters are separated from the 3' end of the transcription terminators by no more than 2000 nucleotides, preferably no more than 1000 nucleotides, more preferably no more than 500 nucleotides, even more preferably no more than 200 nucleotides, especially preferably no more than 100 nucleotides, more especially preferably no more than 50 nucleotides, even more especially preferably no more than 20 nucleotides, particularly preferably no more than 10 nucleotides, more particularly preferably no more than 6 nucleotides.

FIG. 1(c) illustrates schematically a further DNA construct according to the invention which is a plasmid vector comprising two opposable promoters (a) and (b) flanking an inter-promoter region (c). In this embodiment one terminator (in this case (f)) is positioned within the (c) and the other (e) is positioned outside (c). Again, (e) terminates transcription initiated by (a) and (f) terminates transcription initiated by (b). This arrangement may provide a useful solution to the problem of one of the terminators interfering with polymerase activity in the other direction (e.g. (f) interferes with (b) initiated transcription). This vector essentially provides the same advantages as the vector variations shown in FIG. 1(a) and FIG. 1(b) over the prior art. The relatively small difference in the length of the transcript due to the transcription of one of the promoters will not significantly affect the efficacy in RNAi systems. This more particularly the case when the terminator that is located outside of the inter-promoter region (c) is at close proximity of the promoter, as defined above.

FIGS. 1(d) and 1(e) illustrate schematically two further DNA constructs according to the invention which are both plasmid vectors comprising two opposable promoters (a) and (b) flanking an inter-promoter region (c). These embodiments comprise a single terminator only. In the arrangement shown in FIG. 1(d) a single terminator (e) which terminates transcription from (a) is placed outside of (c). The placement of the terminator outside of the inter-promoter region allows the use of both a bi-directional terminator or a uni-directional terminator in this system. In the embodiment shown in FIG. 1(d), (e) is placed within the (c) and should therefore preferably be a uni-directional terminator.

Further embodiments of the DNA construct according to the invention are illustrated schematically in FIGS. 2(b) to 2(e).

These embodiments are all plasmid cloning vectors, based upon the optimal arrangement of promoters and terminators shown in FIG. 1(a), and described above, containing cloning sites to facilitate the insertion of a DNA fragment into the at least one cloning site.

These embodiments are all plasmid cloning vectors, based upon the optimal arrangement of promoters and terminators shown in FIG. 1(a), containing cloning sites to facilitate the insertion of a target DNA fragment into the inter-promoter region.

FIG. 2(a), which is a schematic representation of a prior art cloning vector, is included for comparison purposes. This vector comprises two opposable promoters (a) and (b), which may be identical or different, flanking a multi-cloning site (MCS).

FIG. 2(b) illustrates a first type of plasmid cloning vector according to the invention. The vector contains a first opposable promoter (a) and a second opposable promoter (b) flanking an inter-promoter region. The inter-promoter region can further be defined as: the DNA region between the 3' end of the first promoter and the 3' end of the second promoter, and which is downstream of the first promoter, and which is downstream of the second promoter, and which preferably does not contain the 5' end of the first promoter and of the second promoter. The inter-promoter region further comprises terminators (e) and (f) flanking a multi-cloning site MCS. The MCS comprises at least one individual restriction site, and preferably more than one restriction site as known in the art, any of which may be used for insertion of a DNA fragment.

FIG. 2(c) illustrates a further type of plasmid cloning vector according to the invention. This vector again contains opposable promoters (a) and (b) flanking an inter-promoter region comprising terminators (e) and (f). In this embodiment, (a) and (b) flank a cloning site which is adapted for facilitated cloning of PCR fragments, comprising a stuffer DNA flanked by two identical restriction sites, in this case BstXI sites. The specific sequence of the stuffer DNA is not essential, provided that said stuffer DNA does not interfere with the desired effect and/or the desired activity of the DNA constructs of the invention. A specific example of a vector according to this aspect of the invention described herein is plasmid pGN29.

The cloning of PCR products using BstXI recognition sites and BstXI adaptors is generally known in the art. The BstXI adaptors are commercially obtained, such as from Invitrogen (Groningen, the Netherlands). These adaptors are non-palindromic adapters designed for easier and efficient cloning of PCR products into vectors. These use of these adaptors reduces the concatamerization of adapters or insert DNA by having non-complementary (CACA) overhangs. The stuffer DNA is included merely to allow easy differentiation between BstXI cut and uncut vector on the basis of size. Its precise length and sequence are not of importance.

FIG. 2(d) illustrates a further type of plasmid cloning vector according to the invention. This vector again contains opposable promoters (a) and (b) flanking an inter-promoter region comprising terminators (e) and (f). In this embodiment, (a) and (b) flank a cloning site which facilitates "High Throughput" cloning based on homologous recombination rather than restriction enzyme digestion and ligation. As shown schematically in FIG. 2(d), the cloning site comprises attR1 and attR2 recombination sites from bacteriophage lambda flanking a gene which is lethal to *E. coli*, in this case the ccdB gene.

An alternative cloning method of DNA fragments into this vector,(not shown in FIG. 2(d)), consists of a variant of this vector, wherein the ccdB DNA sequence further comprises at least one unique restriction site, preferably the at least unique restriction site is a blunt-end restriction site, such as a SrfI restriction site. Insertion of a DNA fragment in the at least one unique restriction site, results in inactivation of the ccdB gene, and hence in inactivation of the lethal ccdB gene product.

A further variant of a vector a shown in FIG. 2(d) in which the attR1 and the attR2 are not present. Such a vector comprises at least one cloning site, said at least one cloning site consisting of a ccdB sequence, said ccdB sequence further comprising at least one unique restriction site, preferably the at least unique restriction site is a blunt-end restriction site, such as a SrfI restriction site. Insertion of a DNA fragment in the at least one unique restriction site, results in inactivation of the ccdB gene, and hence in inactivation of the lethal ccdB gene product.

These cloning sites comprising the ccdB nucleotide sequence and/or the attR sites (R1 and/or R2) are derived from the Gateway™ cloning system commercially available from Life Technologies, Inc. The Gateway™ cloning system has been extensively described by Hartley et al. in WO 96/40724 (PCT/US96/10082). A specific example of a vector according to this aspect of the invention described herein is pGN39.

FIGS. 2(e) and 2(f) illustrate a still further type of plasmid cloning vector according to the invention. This vector again contains opposable promoters (a) and (b) flanking an inter-promoter region (c) comprising terminators (e) and (f). In the embodiment shown in FIG. 2(e), terminators (e) and (f) flank a cloning site which facilitates "high throughput" cloning of PCR products by TA™ cloning. This cloning site comprises a stuffer DNA flanked by two identical restriction sites for an enzyme which generates overhanging T nucleotides. In this case the restriction sites are XcmI sites, but other sites which are cleaved to generate overhanging T nucleotides could be used with equivalent effect. The overhanging T nucleotides facilitate cloning of PCR products which have a overhanging A nucleotide. This principle is known as TA™ cloning. The cut vector with overhanging T nucleotides can be "topomerized" to generate a cloning vector of the type shown schematically in FIG. 2(f), by linking the enzyme topoisomerase to the overhanging T nucleotides. The resulting vector also facilitates the cloning of PCR products by the principle known as TOPO™ cloning.

Both the TOPO™ and TA™ cloning systems, although not for the vectors described in this invention, are commercially available from Invitrogen. The TOPO™ cloning system has extensively been described by Shuman in WO 96/19497 (PCT/US95/16099). The TA™ cloning system has extensively been described by Hernstadt et al. in WO 92/06189 (PCT/US91/07147).

It will be readily appreciated by the skilled reader that whilst FIGS. 2(b)-2(f) illustrate the inclusion of different cloning sites into a vector of the type illustrated in FIG. 1(a), these cloning sites could be included into any of the DNA constructs of the invention, including those illustrated schematically in FIGS. 1(b) to 1(e)

Application of the DNA Constructs of the Invention in RNAi Technology.

As aforementioned, a major application of the DNA constructs/vectors of the invention is in the production of double stranded RNA for use in RNAi technology. In particular, the constructs are useful in in vivo RNAi protocols in the nematode worm *C. elegans*.

In *C. elegans*, RNAi has traditionally been performed by injection dsRNA into the worm. Fire et al. describes these methods extensively in International Application No. WO 99/32619. In short, both strands of RNA are produced in vitro using commercially available in vitro transcription kits. Both strands of RNA are allowed to form dsRNA, after which the dsRNA is injected into *C. elegans*.

The new vector system developed by the present inventors is a drastic improvement on this traditional method. First, the RNA can be produced in one step, for instance by using two identical promoters such as in the vector pGN9. Second, and more important, due to the presence of terminators the transcripts, and hence the formed dsRNA, will be more specific as only the cloned target fragment will be transcribed. This will result in a more efficient RNAi.

A further method to perform RNAi experiments in *C. elegans* has been described by Plaetinck et al. in WO 00/01846. In this method *C. elegans* worms are fed with bacteria which produce dsRNA. The dsRNA passes the gut barrier of the worm and induces the same RNAi as if the dsRNA has been injected. For these experiments, the preferred *E. coli* strain is HT115 (DE3), and the preferred *C. elegans* strain is nuc-1;gun-1. The improved vectors provided by the invention also improve the efficiency of RNAi in this method, as shown in the example below, as only effective dsRNA is produced.

Another method to perform RNAi has also been described by Plaetinck et al. in WO 00/01846. In short, this method is based on the production of dsRNA in the worm itself. This can be done by using worm promoters in the described vectors, or by using a transgenic worm expressing a polymerase specific for non-*C. elegans* promoters present in the vector, such that this polymerase drives transcription of the dsRNA. The promoters will preferentially be selected from the known bacteriophage RNA promoters, such as T7 or T3 or SP6 RNA promoters, which provide the advantage of a high level of transcription dependent only on the binding of the cognate polymerase.

Plasmid vector DNA can be introduced into the worm by several methods. First, the DNA can be introduced by the traditional injection method (Methods in Cell Biology, Vol 48, *C. elegans* Modern Biological Analysis of an organism, ed. by Epstein and Shakes). Second, the DNA can be introduced by DNA feeding. As has been shown by Plaetinck et al. in WO 00/01846, plasmid DNA can be introduced into the worm by feeding the worm with an *E. coli* strain that harbors the plasmid. Preferentially the *E. coli* strain is OP50, or MC1061 or HT115 (DE3) but any other strain would suit for this purpose. The *C. elegans* strain is preferentially a nuc-1 mutant strain or a nuc-1; gun-1 strain. The plasmid DNA from the *E. coli* passes the gut barrier and is introduced into the nematode, resulting in the expression of dsRNA. As with the other RNAi methods described above, the use of the new vector system will enhance the RNAi by the production of only specific dsRNA.

The invention will be further understood with reference to the following experimental Examples, together with FIGS. 3-17.

EXAMPLES

Example 1

Vector Construction

The starting point for construction of the vectors exemplified herein was plasmid pGN1. This plasmid, described in the applicant's co-pending International Application No. WO 00/01846, contains two opposable T7 promoters flanking a multi-cloning site.

Vector construction was carried out according to standard molecular biology techniques known in the art and described, for example, in F. M. Ausubel et al. (eds.), *Current Protocols in Molecular Biology*, John Wiley & Sons, Inc. (1994).

1) Construction of pGN9 pGN1 was first digested with restriction enzymes EcoRI and KpnI. Oligonucleotides oGN27 (SEQ ID NO:3) and oGN28 (SE ID NO:4) (FIG. 7) were annealed to generate a double stranded fragment which was then ligated into the EcoRI/KpnI cut vector. The resulting plasmid was re-digested with XbaI and HindIII. Oligonucleotides oGN29 (SEQ ID NO:5) and oGN30 (SEQ ID NO:6) were annealed to generate a double-stranded fragment which was then annealed into the XbaI/HindIII cut vector. The resulting vector was designated pGN9 (FIGS. 4 and 10; SEQ ID NO:8).

2) Construction of Further Cloning Vectors pGN29 (FIG. 9(*a*); FIG. 11; SEQ ID NO:9) was generated by replacing the MCS in pGN9 with a stuffer DNA flanked by BstXI sites. BstXI adapters are commercially available from Invitrogen (Groningen, the Netherlands).

pGN39 (FIG. 9(*b*); FIG. 12; SEQ ID NO:39) was generated by following steps; pGN29 was digested with BsTXI. BstXI adapters (Invitrogen, Groningen, The Netherlands) were ligated to Cassette A provided by the GATEWAY™ system (Life Technologies, Inc.). Cassette A contains attR1, CmR, ccda, ccdB, attR2. The Cassette A with the adapters were then ligated into the digested pGN29, resulting in pGN39A. pGN39A contains a unique SrfI site in the ccdB gene.

The TopoRNAi vector (FIG. 9(*c*); FIG. 13; SEQ ID NO:11) was generated in the following way; pGN29 was digested with BstXI. Using PCR with the primers oGN103 (SEQ ID NO:14) and oGN104 (SEQ ID NO:15) and template pCDM8 (Invitrogen, Groningen, The Netherlands), a stuffer was generated (SEQ ID NO: 20) which includes XcmI sites. Onto the PCR product, BstXI adapters were ligated, and the resulting ligation product was ligated in the BstXI digested pGN29 vector resulting in the TopoRNAi vector.

```
oGN103 (SEQ ID NO:14):
5' TACCAAGGCTAGCATGGTTTATCACTGATAAGTTGG 3' oGN104 (SEQ ID NO:15):
5' TACCAAGGCTAGCATGGGCCTGCCTGAAGGCTGC 3'
``` pGN49A (SEQ ID NO:12) was constructed to insert an additional unique non-blunt restriction site and to delete the CmR gene from pGN39. Overlap PCR was used. A first PCR was performed with primers oGN126 (SEQ ID NO:16) and oGN127 (SEQ ID NO:17) and PGN39A as template. Using primers oGN128 (SEQ ID NO:18) and OGN129 (SEQ ID NO:19) and the same template a second fragment was generated. Overlap PCR using the resulting fragments and primers oGN126P and oGN129P resulted in a final PCR product. To this final PCR product, BstXI adapters were ligated, and the ligation product was ligated into pGN29 digested with BstXI. The resulting vector was designated pGN49A.

A control vector was generated to test the efficiency of the pGN49A cloning vector, such vector should contain the T7 promoters, but not the T7 terminators. For this, the XbaI insert of pGN49A was isolated and cloned in pGN1 digested with the same restriction enzyme. The resulting vector was designated pGN59A (SEQ ID NO:13).

```
oGN126 (SEQ ID NO:16):
pGATCTGGATCCGGCTTACTAAAAGCCAGATAACAGTATGC oGN127 (SEQ ID NO:17):
GGAGACTTTATCGCTTAAGAGACGTGCACTGGCCAGGGGGATCACC oGN128 (SEQ ID NO:18):
CCAGTGCACGTCTCTTAAGCGATAAAGTCTCCCGTGAACTTTACCCGGTGG oGN129 (SEQ ID NO:19)
pGCTGTGTATAAGGGAGCCTGACATTTATATTCCCCAG
```

Example 2

To Illustrate the Usefulness of the Improved Vectors in RNA.

This experiment was designed to illustrate the improved efficiency of the improved vectors of this invention in double-stranded RNA inhibition, as compared to the vectors known from the prior art. A significant increase on the efficacy of the system could be expected, as more effective dsRNA was produced and hence RNAi performed better. The experimental system for this proof of concept experiment was to measure *C. elegans* rescue at 25° C. in nuc-1/pha-1(e2123)ts *C. elegans* mutants by RNAi of sup35 using dsRNA feeding of pGN-2 (–terminator) and pGN-12 (+terminator), with PGN-1 (empty vector) as a control and dilutor. The pha-1 ts/sup-35 mutation has extensively been described by Schnabel in WO 99/49066.

The nuc-1 mutation in *C. elegans* provides for a *C. elegans* strain exhibiting better uptake abilities, such as the uptake of the dsRNA complexes than wild type *C. elegans*. This mutant is deleted in the major DNAse enzymes, and inventors have proven in earlier co-pending applications that this *C. elegans* strain results in enhanced RNAi by feeding the nematode with dsRNAs.

The pha-1(e2123)ts mutation provides a mutant C. elegans strain with a phenotype of survival at 15° C. and lethality at 25° C. This lethality is suppressible by the inhibition of sup-35 expression. RNAi of sup-35 should thus facilitate the rescue of pha-1(e2123)ts at 25° C. The vectors of the present invention, when expressing dsRNA from sup-35, should increase the efficacy of sup-35 RNAi in rescuing pha-1(e2123)ts mutants at 25° C., compared to vectors that do not contain the terminators.

Vector pGN1 was used as empty vector. Vector pGN2 (−terminator) is a vector harboring sup-35 DNA and expressing sup-35 dsRNA when introduced in the appropriate host, the vector has no transcriptional terminators inserted. Vector pGN12 (+terminator) is a vector as described above, containing the transcriptional terminators, and hence resulting in improved dsRNA production when introduced into an appropriate host. Thus, this vector has two unidirectional transcriptional terminators, both placed inside of the inter-promoter region, and flanking the sup-35 fragment. Use of the latter vector was expected to increase the efficacy of the system, here meaning a better rescue (survival) of pha-1(e2123)ts mutants at 25° C.

Experimental Conditions 12-well micro-titer plates were filled with approximately 2 ml of NGM agar per well. (1 liter of NGM agar: 15 g Agar, 1 g peptone, 3 g NaCl, 1 ml cholesterol solution (5 mg/ml in EtOH), with sterile addition after autoclaving of 9.5 ml 0.1M $CaCl_2$, 9.5 ml 0.1 ml $MgSO_4$, 25 ml 1M $KH_2PO_4$/$K_2HPO_4$ buffer pH 6, ampicillin (100 μg/l), 5 ml 0,1 M IPTG and 5 ml nystatin solution (dissolved 10 mg/ml in 1:1 EtOH:$CH_3COONH_4$ 7.5 M)

The dried plates were spotted with approximately 50 μl of an overnight culture of bacteria HT115 (DE3) (Fire A, Carnegie Institution, Baltimore, Md.) transformed with the plasmids. Individual nematodes at the L4 growth stage were then placed in single wells at day 1. In each well 1 nematode was placed (P1). At day two, the P1 nematodes were placed to a new well and left to incubate for a day. The same procedure was repeated at day 3. All plates were further incubated at 25° C. to allow offspring to be formed. Sup35 RNAi induced survival (rescue) as was measured by counting the offspring.

Results

RNAi experiment in C. elegans nuc-1/pha-1(e2123)ts mutants by feeding with E. coli expressing sup-35 dsRNA.

Set Up:
pGN1 as control
pGN2 (sup 35−Term.)
pGN12 (sup 35+Term.)
pGN2+pGN1 dilutions ½, ¼, ⅛, 1/16, 1/32
pGN12+pGN1 dilutions ½, ¼, ⅛, 1/16, 1/32

Conditions:
Incubation temperature 25° C.

Readout:

| Count offspring (adult hermaphrodites) | | | | |
|---|---|---|---|---|
| pGN1 (control) | | | | |
| Day 1 | 0 | 0 | 0 | 0 |
| Day 2 | 0 | 0 | 0 | 0 |
| Day 3 | 0 | 0 | 0 | 0 |
| pGN2 (undiluted) | | | | pGN12 (undiluted) |
| Day 1 | 12 | 4 | 48 | 32 | Day 1 | 16 | 29 | 37 | 14 |
| Day 2 | 24 | 23 | 80 | 85 | Day 2 | 27 | 22 | 57 | 2 |
| Day 3 | 5 | 0 | 9 | 16 | Day 3 | 1 | 2 | 4 | 1 |
| pGN 2 + 1, ½ dilution | | | | pGN 12 + 1, ½ dilution |
| Day 1 | 0 | 7 | 0 | 2 | Day 1 | 22 | 28 | 103 | 61 |
| Day 2 | 9 | 10 | 0 | 3 | Day 2 | 36 | 45 | 53 | 40 |
| Day 3 | 0 | 2 | 0 | 0 | Day 3 | 3 | 3 | 25 | 1 |
| pGN 2 + 1, ¼ dilution | | | | pGN 12 + 1, ¼ dilution |
| Day 1 | 28 | 23 | 0 | 0 | Day 1 | * | 6 | 36 | 5 |
| Day 2 | 6 | 3 | 0 | 0 | Day 2 |   | 24 | 55 | 3 |
| Day 3 | 0 | 0 | 0 | 0 | Day 3 |   |   |   |   |
| pGN 2 + 1, ⅛ dilution | | | | pGN 12 + 1, ⅛ dilution |
| Day 1 | 0 | 0 | 4 | 0 | Day 1 | 31 | 12 | 16 | 38 |
| Day 2 | 0 | 0 | 11 | 0 | Day 2 | 4 | 5 | 37 | 4 |
| Day 3 | 0 | 0 | 0 | 0 | Day 3 | 0 | 0 | 2 | 1 |
| pGN 2 + 1, 1/16 dilution | | | | pGN 12 + 1, 1/16 dilution |
| Day 1 | 0 | 0 | 0 | 0 | Day 1 | 1 | 0 | 0 | 0 |
| Day 2 | 0 | 0 | 0 | 1 little | Day 2 | 2 | 0 | 0 | 1 |
| Day 3 | 0 | 0 | 0 | 0 | Day 3 | 0 | 1 | 1 | 1 |
| pGN 2 + 1, 1/32 dilution | | | | pGN 12 + 1, 1/32 dilution |
| Day 1 | 0 | 0 | 0 | 0 | Day 1 | 0 | 0 | 1 | 0 |
| Day 2 | 0 | 0 | 0 | 0 | Day 2 | 0 | L2 | 3 | 0 |
| Day 3 | 0 | 0 | 0 | 0 | Day 3 | 2 | 0 | L3-L4 | 0 |

* mother died

Conclusions

As expected, worms fed by bacteria harboring pGN1, did not result in the viable offspring, due to the lethal effect of the pha-1 mutation at this temperature.

Feeding the nematodes with E. coli harboring pGN2 or pGN12 both result in viable offspring. This is due to the feeding of the worm with dsRNA from sup-35. The remarkable difference between the two feeding experiments can be seen in the dilution series. When diluting the bacteria harboring pGN2 with bacteria harboring pGN1, the number of offspring diminishes drastically, even at a low dilution of one to two. This dilution series indicates that high levels of dsRNA are needed to have a proper RNAi induction. In the feeding experiment with bacteria harboring pGN12, significant offspring is still observed at a dilution of one to eight. This indicates that in the bacteria harboring pGN12, much more effective dsRNA is formed.

This experiment clearly shows that the addition of terminator sequences in vectors to express dsRNA as described above provide a significant advantage in the generation of RNAi.

Example 3

Comparison of RNAi Efficiency of Vectors with and without T7 Terminators(pGN49 vs pGN59)

Three different genes have been cloned in the vectors pGN49A and pGN59A. The cloning was performed by amplifying the gene fragments with PfuI DNA polymerase producing blunt ends, facilitating cloning in these vectors. These PCR fragments were cloned into the vectors digested with SrfI. Correct fragment insertion of the clones was checked by PCR. The fragments are chosen such that ds expression and RNAi results in a lethal phenotype of the offspring. This procedure allows fast and easy comparison of the efficiency of the two vectors pGN49 and pGN59 in RNAi.

| plasmid | Gene (acedb) | Vector backbone |
|---|---|---|
| pGW5 | B0511.8 | pGN49A |
| pGW9 | C01G8.7 | pGN49A |
| pGW11 | C47B2.3 | pGN49A |
| pGW17 | B0511.8 | pGN59A |
| pGW21 | C01G8.7 | pGN59A |
| pGW23 | C47B2.3 | pGN59A |

All the plasmids (pGW-series) are transformed in *E. coli* AB301-105 (DE3) bacteria by standard methodology. The bacteria are then grown in LB/amp at 37° C. for 14-18 h. These cultures were centrifuged and the bacterial pellet dissolved in S-complete buffer containing 1 mM IPTG and 100 µg/µl ampicillin.

In 96 well plates containing 100 µl S-complete (containing 1 mM IPTG and 100 µg/µl ampicillin final concentration) and 10 µl of bacteria solution, 3 nematodes were added at each well, the nematodes were at the L1 growth stage.

The plates were incubated at 25° C. for 5-6 days. Each day the plates were inspected for development of the larvae and the production of F1 offspring.

Results

The RNAi was performed in eight-fold for each constructed plasmid. The results show that when T7 terminators are inserted into the vector backbone, the expected phenotype gives a 100% occurrence. When T7 terminators are not used the reproducibility can decrease up to 50%. As in the previous experiment, the results show that the addition of terminators significantly enhances RNAi performance.

| | DNA fragment | | | | | |
|---|---|---|---|---|---|---|
| | B0511.8 | B0511.8 | C01G8.7 | C01G8.7 | C47B2.3 | C47B2.3 |
| Vector | pGN49A | pGN59A | PGN49A | pGN59A | pGN49A | pGN59A |
| Resulting plasmid | PGW5 | PGW17 | PGW9 | PGW21 | PGW11 | PGW23 |
| Percentage lethal | 100 | 75 | 100 | 87.5 | 100 | 50 |
| Percentage offspring | 0 | 25 | 0 | 12.5 | 0 | 50 |

```
PCR fragment generated by the primers oGN103 and
    oGN104 on template pCDM8 (SEQ ID NO:20)

taccaaggct agcatggttt atcactgata agttgg ataagttggt ggacatatta tgtttatcag tgataaagtg tcaagcatga caaagttgca gccgaataca gtgatccgtg ccggccctgg actgttgaac gaggtcggcg tagacggtct gacgacacgc aaactggcgg aacggttggg ggtgcagcag ccggcgcttt actggcactt caggaacaag cgggcgctgc tcgacgcact ggccgaagcc atgctggcgg agaatcatac gcttcggtgc cgagagccga cgacgactgg cgctcatttc tgatcgggaa tcccgcagct tcaggcaggc ccatgctagc cttggtacca gcacaatgg
```

| Overlap PCR Fragment, which was used to generate pGN49A (SEQ ID NO:21) |
|---|
| gatctggatccggcttactaaaagccagataacagtatgcgtatttgcgc |
| gctgattttgcggtataagaatatatactgatatgtatacccgaagtat |
| gtcaaaaagaggtgtgctatgaagcagcgtattacagtgacagttgacag |
| cgacagctatcagttgctcaaggcatatatgatgtcaatatctccggtct |
| ggtaagcacaaccatgcagaatgaagcccgtcgtctgcgtgccgaacgct |
| ggaaagcggaaaatcaggaagggatggctgaggtcgcccggtttattgaa |
| atgaacggctcttttgctgacgagaacagggactggtgaaatgcagttta |
| aggtttacacctataaaagagagagccgttatcgtctgtttgtggatgta |
| cagagtgatattattgacacgcccgggcgacggatggtgatcccctggc |
| cagtgcacgtctcttaagcgataaagtctcccgtgaactttacccggtgg |
| tgcatatcggggatgaaagctggcgcatgatgaccaccgatatggccagt |

-continued

| Overlap PCR Fragment, which was used to generate pGN49A (SEQ ID NO:21) |
|---|
| gtgccggtctccgttatcggggaagaagtggctgatctcagccaccgcga |
| aaatgacatcaaaaacgccattaacctgatgttctggggaatataaatgt |
| caggctcccttatacacagc |

Other aspects of the invention will be clear to the skilled artisan and need not be repeated here. Each reference or publication cited herein is incorporated by reference in its entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A DNA construct that produces double stranded RNA comprising:
   a) a first promoter and
   b) a second promoter,
   in which the first and second promoter are in opposite orientation to each other and define:
   c) an inter-promoter region positioned downstream of the 3' end of the first promoter and downstream of the 3' end of the second promoter;
   and which DNA construct further comprises:
   d) at least one cloning site positioned in the inter-promoter region; and
   e) a first transcription terminator, positioned, as seen from the 3' end of the first promoter, downstream of the first promoter and downstream of the at least one cloning site, wherein the first transcription terminator is operably linked to the first promoter.

2. A DNA construct according to claim 1, further comprising:
   f) a second transcription terminator positioned, as seen from the 3' end of the second promoter, downstream of the second promoter and downstream of the at least one cloning site,
   wherein the second transcription terminator is operably linked to the second promoter.

3. A DNA construct according to claim 1, in which the first transcription terminator is positioned in the inter-promoter region.

4. A DNA construct according to claim 1, in which the first transcription terminator is positioned, as seen from the 3' end of the first promoter, downstream of the first promoter, downstream of the at least one cloning site, and downstream of the 5' end of the second promoter.

5. A DNA construct according to claim 2, in which the second transcription terminator is positioned in the inter-promoter region.

6. A DNA construct according to claim 2, in which the second transcription terminator is positioned, as seen from the 3' end of the second promoter, downstream of the second promoter, downstream of the at least one cloning site, and downstream of the 5' end of the first promoter.

7. A DNA construct according to claim 4, in which the 3' end of the first transcription terminator is separated from the 5' end of the second promoter by no more than 2000 nucleotides.

8. A DNA construct according to claim 7, in which the 3' end of the second transcription terminator is separated from the 5' end of the first promoter by no more than 500 nucleotides.

9. A DNA construct according to claim 1 wherein the first and the second promoter are identical.

10. A DNA construct according to claim 1 wherein the first and the second promoter are non-identical.

11. A DNA construct according to claim 8 wherein the first promoter and the second promoter are independently chosen from T7, T3 or SP6 promoters.

12. A construct according to claim 1 wherein the cloning site comprises at least one restriction site.

13. A DNA according to claim 12 wherein the cloning site comprises at least two restriction sites flanking a sequence of DNA.

14. A DNA construct according to claim 13 wherein the at least two restriction sites are identical.

15. A DNA construct according to claim 12 wherein the at least one restriction site are BstXI sites.

16. A DNA construct according to claim 12 wherein the at least one restriction sites are XcmI sites.

17. A DNA construct according to claim 1 wherein the cloning site further comprises attR1 and attR2 recombination sequences.

18. A DNA construct according to claim 1 wherein the cloning site further comprises a ccdB nucleotide sequence.

19. A DNA construct according to claim 18 wherein the ccdB nucleotide sequence further comprises at least one unique restriction site.

20. A DNA construct according to claim 19 wherein the at least one unique restriction site is at least one blunt-end restriction site.

21. A DNA construct according to claim 20 wherein the at least one blunt-end restriction site is at least one SrfI site.

22. A DNA according to claim 2 which further comprises:
(g) a DNA fragment inserted in the at least one cloning site.

23. A DNA construct according to claim 1 which is a plasmid or vector.

24. A DNA construct according to claim 7, in which the 3' end of the second transcription terminator is separated from the 5' end of the first promoter by no more than 200 nucleotides.

25. A method for the production of double-stranded RNA for RNA inhibition comprising using the DNA construct of any of claims 1-23 or claim 24 for the expression of double stranded RNA inserted in the cloning site.

26. A bacterial strain harbouring the DNA construct according to claim 1.

27. A bacterial strain according to claim 26, wherein said bacterial strain is an *E. coli* strain.

28. A method for the production of double-stranded RNA for RNA inhibition comprising using the bacterial strain of claim 26 or claim 27 for the expression of double stranded RNA inserted in the cloning site.

* * * * *

SEQUENCE LISTING

```
<160> NUMBER OF SEQ ID NOS: 21

<210> SEQ ID NO 1
<211> LENGTH: 160
<212> TYPE: DNA
<213> ORGANISM: Artificial Sequence
<220> FEATURE:
<223> OTHER INFORMATION: Description of Artificial Sequence: Fragment of
                        pGN1 containing opposable T7 promoters

<400> SEQUENCE: 1
ttgtaatacg actcactata gggcgaattc gagctcggta cccggggatc ctctagagtc      60
gaaagcttct cgccctatag tgagtcgtat tacagcttga gtattctata gtgtcaccta     120
aatagcttgg cgtaatcatg gtcatagctg tttcctgtgt                           160

<210> SEQ ID NO 2
<211> LENGTH: 49
<212> TYPE: DNA
<213> ORGANISM: Artificial Sequence
<220> FEATURE:
<223> OTHER INFORMATION: Description of Artificial Sequence: DNA
                        sequence containing a T7 terminator

<400> SEQUENCE: 2
actagcataa ccccttgggg cctctaaacg ggtcttgagg ggttttttg                  49

<210> SEQ ID NO 3
<211> LENGTH: 70
<212> TYPE: DNA
<213> ORGANISM: Artificial Sequence
<220> FEATURE:
<223> OTHER INFORMATION: Description of Artificial Sequence:
                        Oligonucleotide oGN27

<400> SEQUENCE: 3
aattcaaaaa acccctcaag acccgtttag aggccccaag gggttatgct agtgaattct      60
gcagcggtac                                                            70
```

```
<210> SEQ ID NO 4
<211> LENGTH: 62
<212> TYPE: DNA
<213> ORGANISM: Artificial Sequence
<220> FEATURE:
<223> OTHER INFORMATION: Description of Artificial Sequence:
      Oligonucleotide oGN28

<400> SEQUENCE: 4
cgctgcagaa ttcactagca taacccctttg gggcctctaa acgggtcttg aggggttttt    60
tg                                                                    62

<210> SEQ ID NO 5
<211> LENGTH: 65
<212> TYPE: DNA
<213> ORGANISM: Artificial Sequence
<220> FEATURE:
<223> OTHER INFORMATION: Description of Artificial Sequence:
      Oligonucleotide oGN29

<400> SEQUENCE: 5
ctagacgcgt aagcttacta gcataacccc ttggggcctc taaacgggtc ttgaggggtt    60
ttttg                                                                 65

<210> SEQ ID NO 6
<211> LENGTH: 65
<212> TYPE: DNA
<213> ORGANISM: Artificial Sequence
<220> FEATURE:
<223> OTHER INFORMATION: Description of Artificial Sequence:
      Oligonucleotide oGN30

<400> SEQUENCE: 6
agctcaaaaa acccctcaag acccgtttag aggccccaag gggttatgct agtaagctta    60
cgcgt                                                                 65

<210> SEQ ID NO 7
<211> LENGTH: 230
<212> TYPE: DNA
<213> ORGANISM: Artificial Sequence
<220> FEATURE:
<223> OTHER INFORMATION: Description of Artificial Sequence: Fragment of
      plasmid pGN9 containing opposable T7 promoters
      and T7 transcription terminators

<400> SEQUENCE: 7
ttgtaatacg actcactata gggcgaattc aaaaaacccc tcaagacccg tttagaggcc    60
ccaaggggtt atgctagtga attctgcagg gtacccgggg atcctctaga cgcgtaagct   120
tactagcata accccttggg gcctctaaac gggtcttgag gggttttttg agcttctcgc   180
cctatagtga gtcgtattac agcttgagta ttctatagtg tcacctaaat              230

<210> SEQ ID NO 8
<211> LENGTH: 3323
<212> TYPE: DNA
<213> ORGANISM: Artificial Sequence
<220> FEATURE:
<223> OTHER INFORMATION: Description of Artificial Sequence: Plasmid
      pGN9

<400> SEQUENCE: 8
gagtgcacca tatgcggtgt gaaataccgc acagatgcgt aaggagaaaa taccgcatca    60
```

-continued

| | |
|---|---|
| ggcgaaattg taaacgttaa tattttgtta aaattcgcgt taaatatttg ttaaatcagc | 120 |
| tcatttttta accaataggc cgaaatcggc aaaatcccct ataaatcaaa agaatagacc | 180 |
| gagatagggt tgagtgttgt tccagtttgg aacaagagtc cactattaaa gaacgtggac | 240 |
| tccaacgtca aagggcgaaa aaccgtctat cagggcgatg gcccactacg tgaaccatca | 300 |
| cccaaatcaa gttttttgcg gtcgaggtgc cgtaaagctc taaatcggaa ccctaaaggg | 360 |
| agcccccgat ttagagcttg acggggaaag ccggcgaacg tggcgagaaa ggaagggaag | 420 |
| aaagcgaaag gagcgggcgc tagggcgctg gcaagtgtag cggtcacgct gcgcgtaacc | 480 |
| accacacccg ccgcgcttaa tgcgccgcta cagggcgcgt ccattcgcca ttcaggctgc | 540 |
| gcaactgttg ggaagggcga tcggtgcggg cctcttcgct attacgccag ctggcgaaag | 600 |
| ggggatgtgc tgcaaggcga ttaagttggg taacgccagg ttttcccag tcacgacgtt | 660 |
| gtaaaacgac ggccagtgaa ttgtaatacg actcactata gggcgaattc aaaaaacccc | 720 |
| tcaagacccg tttagaggcc caagggggtt atgctagtga attctgcagg gtacccgggg | 780 |
| atcctctaga cgcgtaagct tactagcata accccttggg gcctctaaac gggtcttgag | 840 |
| gggttttttg agcttctcgc cctatagtga gtcgtattac agcttgagta ttctatagtg | 900 |
| tcacctaaat agcttggcgt aatcatggtc atagctgttt cctgtgtgaa attgttatcc | 960 |
| gctcacaatt ccacacaaca tacgagccgg aagcataaag tgtaaagcct ggggtgccta | 1020 |
| atgagtgagc taactcacat taattgcgtt gcgctcactg cccgctttcc agtcgggaaa | 1080 |
| cctgtcgtgc cagctgcatt aatgaatcgg ccaacgcgcg gggagaggcg gtttgcgtat | 1140 |
| tgggcgctct tccgcttcct cgctcactga ctcgctgcgc tcggtcgttc ggctgcggcg | 1200 |
| agcggtatca gctcactcaa aggcggtaat acggttatcc acagaatcag gggataacgc | 1260 |
| aggaaagaac atgtgagcaa aaggccagca aaaggccagg aaccgtaaaa aggccgcgtt | 1320 |
| gctggcgttt ttcgataggc tccgcccccc tgacgagcat cacaaaaatc gacgctcaag | 1380 |
| tcagaggtgg cgaaacccga caggactata aagataccag gcgtttcccc ctggaagctc | 1440 |
| cctcgtgcgc tctcctgttc cgaccctgcc gcttaccgga tacctgtccg cctttctccc | 1500 |
| ttcgggaagc gtggcgcttt ctcatagctc acgctgtagg tatctcagtt cggtgtaggt | 1560 |
| cgttcgctcc aagctgggct gtgtgcacga accccccgtt cagcccgacc gctgcgcctt | 1620 |
| atccggtaac tatcgtcttg agtccaaccc ggtaagacac gacttatcgc cactggcagc | 1680 |
| agccactggt aacaggatta gcagagcgag gtatgtaggc ggtgctacag agttcttgaa | 1740 |
| gtggtggcct aactacggct acactagaag gacagtattt ggtatctgcg ctctgctgaa | 1800 |
| gccagttacc ttcggaaaaa gagttggtag ctcttgatcc ggcaaacaaa ccaccgctgg | 1860 |
| tagcggtggt ttttttgttt gcaagcagca gattacgcgc agaaaaaaag gatctcaaga | 1920 |
| agatcctttg atcttttcta cggggtctga cgctcagtgg aacgaaaact cacgttaagg | 1980 |
| gattttggtc atgagattat caaaaaggat cttcacctag atccttttaa attaaaaatg | 2040 |
| aagttttaaa tcaatctaaa gtatatatga gtaaacttgg tctgacagtt accaatgctt | 2100 |
| aatcagtgag gcacctatct cagcgatctg tctatttcgt tcatccatag ttgcctgact | 2160 |
| ccccgtcgtg tagataacta cgatacggga gggcttacca tctggcccca gtgctgcaat | 2220 |
| gataccgcga gacccacgct caccggctcc agatttatca gcaataaacc agccagccgg | 2280 |
| aagggccgag cgcagaagtg gtcctgcaac tttatccgcc tccatccagt ctattaattg | 2340 |
| ttgccgggaa gctagagtaa gtagttcgcc agttaatagt ttgcgcaacg ttgttggcat | 2400 |
| tgctacaggc atcgtggtgt cacgctcgtc gtttggtatg gcttcattca gctccggttc | 2460 |

-continued

```
ccaacgatca aggcgagtta catgatcccc catgttgtgc aaaaaagcgg ttagctcctt    2520
cggtcctccg atcgttgtca gaagtaagtt ggccgcagtg ttatcactca tggttatggc    2580
agcactgcat aattctctta ctgtcatgcc atccgtaaga tgcttttctg tgactggtga    2640
gtactcaacc aagtcattct gagaataccg cgcccggcga ccgagttgct cttgcccggc    2700
gtcaatacgg gataatagtg tatgacatag cagaacttta aaagtgctca tcattggaaa    2760
acgttcttcg gggcgaaaac tctcaaggat cttaccgctg ttgagatcca gttcgatgta    2820
acccactcgt gcacccaact gatcttcagc atcttttact ttcaccagcg tttctgggtg    2880
agcaaaaaca ggaaggcaaa atgccgcaaa aaagggaata agggcgacac ggaaatgttg    2940
aatactcata ctcttccttt ttcaatatta ttgaagcatt tatcagggtt attgtctcat    3000
gagcggatac atatttgaat gtatttagaa aaataaacaa ataggggttc cgcgcacatt    3060
tccccgaaaa gtgccacctg acgtctaaga accattatt atcatgacat aacctataa     3120 aaataggcgt atcacgaggc cctttcgtct cgcgcgtttc ggtgatgacg gtgaaaacct    3180
ctgacacatg cagctcccgg agacggtcac agcttgtctg taagcggatg ccggagcag    3240 acaagcccgt cagggcgcgt cagcgggtgt tggcgggtgt cggggctggc ttaactatgc    3300
ggcatcagag cagattgtac tga                                            3323
```

<210> SEQ ID NO 9
<211> LENGTH: 3774
<212> TYPE: DNA
<213> ORGANISM: Artificial Sequence
<220> FEATURE:
<223> OTHER INFORMATION: Description of Artificial Sequence: Plasmid pGN29

<400> SEQUENCE: 9

```
gagtgcacca tatgcggtgt gaaataccgc acagatgcgt aaggagaaaa taccgcatca      60
ggcgaaattg taaacgttaa tattttgtta aaattcgcgt taaatatttg ttaaatcagc     120
tcatttttta accaataggc cgaaatcggc aaaatccctt ataaatcaaa agaatagacc     180
gagatagggt tgagtgttgt tccagtttgg aacaagagtc cactattaaa gaacgtggac     240
tccaacgtca aagggcgaaa aaccgtctat cagggcgatg cccactacg tgaaccatca      300 cccaaatcaa gttttttgcg gtcgaggtgc cgtaaagctc taaatcggaa ccctaaaggg     360 agccccgat ttagagcttg acggggaaag ccggcgaacg tggcgagaaa ggaagggaag      420
aaagcgaaag gagcgggcgc tagggcgctg gcaagtgtag cggtcacgct gcgcgtaacc     480
accacacccg ccgcgcttaa tgcgccgcta cagggcgcgt ccattcgcca ttcaggctgc     540
gcaactgttg ggaagggcga tcggtgcggg cctcttcgct attacgccag ctggcgaaag     600
ggggatgtgc tgcaaggcga ttaagttggg taacgccagg gttttcccag tcacgacgtt     660
gtaaaacgac ggccagtgaa ttgtaatacg actcactata gggcgaattc aaaaaacccc     720
tcaagacccg tttagaggcc ccaaggggtt atgctagtga attctgcagg gtacccgggg     780
atcctctaga gatccctcga cctcgagatc cattgtgctg gcgcggattc tttatcactg     840
ataagttggt ggacatatta tgtttatcag tgataaagtg tcaagcatga caaagttgca     900
gccgaataca gtgatccgtg ccggccctgg actgttgaac gaggtcggcg tagacggtct     960
gacgacacgc aaactggcgg aacggttggg ggtgcagcag ccggcgcttt actggcactt    1020
caggaacaag cggcgctgc tcgacgcact ggccgaagcc atgctggcgg agaatcatac    1080
gcttcggtgc cgagagccga cgacgactgg cgctcatttc tgatcgggaa tcccgcagct    1140
```

-continued

```
tcaggcaggc gctgctcgcc taccgccagc acaatggatc tcgagggatc ttccatacct    1200
accagttctg cgcctgcagg tcgcggccgc gactctctag acgcgtaagc ttactagcat    1260
aaccccttgg ggcctctaaa cgggtcttga ggggttttt gagcttctcg ccctatagtg    1320
agtcgtatta cagcttgagt attctatagt gtcacctaaa tagcttggcg taatcatggt    1380
catagctgtt tcctgtgtga aattgttatc cgctcacaat tccacacaac atacgagccg    1440
gaagcataaa gtgtaaagcc tggggtgcct aatgagtgag ctaactcaca ttaattgcgt    1500
tgcgctcact gcccgctttc cagtcgggaa acctgtcgtg ccagctgcat taatgaatcg    1560
gccaacgcgc ggggagaggc ggtttgcgta ttgggcgctc ttccgcttcc tcgctcactg    1620
actcgctgcg ctcggtcgtt cggctgcggc gagcggtatc agctcactca aaggcggtaa    1680
tacggttatc cacagaatca ggggataacg caggaaagaa catgtgagca aaaggccagc    1740
aaaaggccag gaaccgtaaa aaggccgcgt tgctggcgtt tttcgatagg ctccgccccc    1800
ctgacgagca tcacaaaaat cgacgctcaa gtcagaggtg gcgaaacccg acaggactat    1860
aaagatacca ggcgtttccc cctggaagct ccctcgtgcg ctctcctgtt ccgaccctgc    1920
cgcttaccgg atacctgtcc gcctttctcc cttcgggaag cgtggcgctt tctcatagct    1980
cacgctgtag gtatctcagt tcggtgtagg tcgttcgctc caagctgggc tgtgtgcacg    2040
aaccccccgt tcagcccgac cgctgcgcct tatccggtaa ctatcgtctt gagtccaacc    2100
cggtaagaca cgacttatcg ccactggcag cagccactgg taacaggatt agcagagcga    2160
ggtatgtagg cggtgctaca gagttcttga agtggtggcc taactacggc tacactagaa    2220
ggacagtatt tggtatctgc gctctgctga agccagttac cttcggaaaa agagttggta    2280
gctcttgatc cggcaaacaa accaccgctg gtagcggtgg ttttttttgtt tgcaagcagc    2340 agattacgcg cagaaaaaaa ggatctcaag aagatccttt gatcttttct acggggtctg    2400
acgctcagtg gaacgaaaac tcacgttaag ggattttggt catgagatta tcaaaaagga    2460
tcttcaccta gatccttta aattaaaaat gaagttttaa atcaatctaa agtatatatg    2520
agtaaacttg gtctgacagt taccaatgct taatcagtga ggcacctatc tcagcgatct    2580
gtctatttcg ttcatccata gttgcctgac tccccgtcgt gtagataact acgatacggg    2640
agggcttacc atctggcccc agtgctgcaa tgataccgcg agaccacgc tcaccggctc    2700 cagatttatc agcaataaac cagccagccg aagggccga gcgcagaagt ggtcctgcaa    2760
ctttatccgc ctccatccag tctattaatt gttgccggga agctagagta agtagttcgc    2820
cagttaatag tttgcgcaac gttgttggca ttgctacagg catcgtggtg tcacgctcgt    2880
cgtttggtat ggcttcattc agctccggtt cccaacgatc aaggcgagtt acatgatccc    2940
ccatgttgtg caaaaaagcg gttagctcct tcggtcctcc gatcgttgtc agaagtaagt    3000
tggccgcagt gttatcactc atggttatgg cagcactgca taattctctt actgtcatgc    3060
catccgtaag atgcttttct gtgactggtg agtactcaac caagtcattc tgagaatacc    3120
gcgcccggcg accgagttgc tcttgcccgg cgtcaatacg ggataatagt gtatgacata    3180
gcagaacttt aaaagtgctc atcattggaa aacgttcttc ggggcgaaaa ctctcaagga    3240
tcttaccgct gttgagatcc agttcgatgt aacccactcg tgcacccaac tgatcttcag    3300
catcttttac tttcaccagc gtttctgggt gagcaaaaac aggaaggcaa aatgccgcaa    3360
aaaagggaat aagggcgaca cggaaatgtt gaatactcat actcttcctt tttcaatatt    3420
attgaagcat ttatcagggt tattgtctca tgagcggata catatttgaa tgtatttaga    3480
```

-continued

```
aaaataaaca ataggggtt ccgcgcacat ttccccgaaa agtgccacct gacgtctaag    3540
aaaccattat tatcatgaca ttaacctata aaaataggcg tatcacgagg cccttctgtc    3600
tcgcgcgttt cggtgatgac ggtgaaaacc tctgacacat gcagctcccg gagacggtca    3660
cagcttgtct gtaagcggat gccggagca gacaagcccg tcagggcgcg tcagcgggtg     3720
ttggcgggtg tcggggctgg cttaactatg cggcatcaga gcagattgta ctga          3774
```

<210> SEQ ID NO 10
<211> LENGTH: 5148
<212> TYPE: DNA
<213> ORGANISM: Artificial Sequence
<220> FEATURE:
<223> OTHER INFORMATION: Description of Artificial Sequence: Plasmid pGN39

<400> SEQUENCE: 10

```
taatacgact cactataggg cgaattcaaa aaaccctca agacccgttt agaggcccca      60
aggggttatg ctagtgaatt ctgcagcggt acccggggat cctctagaga tccctcgacc    120
tcgagatcca ttgtgctgga agatcacaa gtttgtacaa aaaagctgaa cgagaaacgt     180
aaaatgatat aaatatcaat atattaaatt agattttgca taaaaaacag actacataat    240
actgtaaaac acaacatatc cagtcactat ggcggccgca ttaggcaccc caggctttac    300
actttatgct tccggctcgt ataatgtgtg gattttgagt taggatccgg cgagattttc    360
aggagctaag gaagctaaaa tggagaaaaa aatcactgga tataccaccg ttgatatatc    420
ccaatggcat cgtaaagaac attttgaggc atttcagtca gttgctcaat gtacctataa    480
ccagaccgtt cagctggata ttacggcctt tttaaagacc gtaaagaaaa ataagcacaa    540
gttttatccg gcctttattc acattcttgc ccgcctgatg aatgctcatc cggaattccg    600
tatggcaatg aaagacggtg agctggtgat atgggatagt gttcacccct gttacaccgt    660
tttccatgag caaactgaaa cgttttcatc gctctggagt gaataccacg acgatttccg    720
gcagtttcta cacatatatt cgcaagatgt ggcgtgttac ggtgaaaacc tggcctattt    780
ccctaaaggg tttattgaga atatgttttt cgtctcagcc aatccctggg tgagtttcac    840
cagttttgat ttaaacgtgg ccaatatgga aacttcttc gccccgtttt tcaccatggg    900
caaatattat acgcaaggcg acaaggtgct gatgccgctg gcgattcagg ttcatcatgc    960
cgtctgtgat ggcttccatg tcggcagaat gcttaatgaa ttacaacagt actgcgatga   1020
gtggcagggc ggggcgtaaa gatctggatc cggcttacta aaagccagat aacagtatgc   1080
gtatttgcgc gctgattttt gcggtataag aatatatact gatatgtata cccgaagtat   1140
gtcaaaaaga ggtgtgctat gaagcagcgt attacagtga cagttgacag cgacagctat   1200
cagttgctca aggcatatat gatgtcaata tctccggtct ggtaagcaca accatgcaga   1260
atgaagcccg tcgtctgcgt gccgaacgct ggaaagcgga aaatcaggaa gggatggctg   1320
aggtcgcccg gtttattgaa atgaacggct cttttgctga cgagaacagg gactggtgaa   1380
atgcagttta aggtttacac ctataaaaga gagagccgtt atcgtctgtt tgtggatgta   1440
cagagtgata ttattgacac gcccgggcga cggatggtga tccccctggc cagtgcacgt   1500
ctgctgtcag ataaagtctc ccgtgaactt taccggtgg tgcatatcgg ggatgaaagc    1560
tggcgcatga tgaccaccga tatggccagt gtgccggtct ccgttatcgg ggaagaagtg   1620
gctgatctca gccaccgcga aaatgacatc aaaaacgcca ttaacctgat gttctgggga   1680
atataaatgt caggctcccct tatacacagc cagtctgcag gtcgaccata gtgactggat   1740
```

```
atgttgtgtt ttacagtatt atgtagtctg ttttttatgc aaaatctaat ttaatatatt      1800
gatatttata tcattttacg tttctcgttc agctttcttg tacaaagtgg tgatctttcc      1860
agcacaatgg atctcgaggg atcttccata cctaccagtt ctgcgcctgc aggtcgcggc      1920
cgcgactcta gacgcgtaag cttactagca taaccccttg gggcctctaa acgggtcttg      1980
aggggttttt tgagcttctc gccctatagt gagtcgtatt acagcttgag tattctatag      2040
tgtcacctaa atagcttggc gtaatcatgg tcatagctgt ttcctgtgtg aaattgttat      2100
ccgctcacaa ttccacacaa catacgagcc ggaagcataa agtgtaaagc ctggggtgcc      2160
taatgagtga gctaactcac attaattgcg ttgcgctcac tgcccgcttt ccagtcggga      2220
aacctgtcgt gccagctgca ttaatgaatc ggccaacgcg ggggagagg cggtttgcgt       2280 attgggcgct cttccgcttc ctcgctcact gactcgctgc gctcggtcgt tcggctgcgg      2340
cgagcggtat cagctcactc aaaggcggta atacggttat ccacagaatc aggggataac      2400
gcaggaaaga acatgtgagc aaaaggccag caaaaggcca ggaaccgtaa aaaggccgcg      2460
ttgctggcgt ttttcgatag gctccgcccc cctgacgagc atcacaaaaa tcgacgctca      2520
agtcagaggt ggcgaaaccc gacaggacta taaagatacc aggcgtttcc ccctggaagc      2580
tccctcgtgc gctctcctgt tccgaccctg ccgcttaccg gatacctgtc gcctttctc      2640 ccttcgggaa gcgtggcgct ttctcatagc tcacgctgta ggtatctcag ttcggtgtag      2700
gtcgttcgct ccaagctggg ctgtgtgcac gaaccccccg ttcagcccga ccgctgcgcc      2760
ttatccggta actatcgtct tgagtccaac ccggtaagac acgacttatc gccactggca      2820
gcagccactg gtaacaggat tagcagagcg aggtatgtag gcggtgctac agagttcttg      2880
aagtggtggc ctaactacgg ctacactaga aggacagtat ttggtatctg cgctctgctg      2940
aagccagtta ccttcggaaa aagagttggt agctcttgat ccggcaaaca aaccaccgct      3000
ggtagcggtg ttttttttgt ttgcaagcag cagattacgc gcagaaaaaa aggatctcaa      3060
gaagatcctt tgatcttttc tacggggtct gacgctcagt ggaacgaaaa ctcacgttaa      3120
gggattttgg tcatgagatt atcaaaaagg atcttcacct agatcctttt aaattaaaaa      3180
tgaagtttta aatcaatcta agtatatat gagtaaactt ggtctgacag ttaccaatgc       3240
ttaatcagtg aggcacctat ctcagcgatc tgtctatttc gttcatccat agttgcctga     3300
ctccccgtcg tgtagataac tacgatacgg gagggcttac catctggccc cagtgctgca      3360
atgataccgc gagacccacg ctcaccggct ccagatttat cagcaataaa ccagccagcc      3420
ggaagggccg agcgcagaag tggtcctgca actttatccg cctccatcca gtctattaat      3480
tgttgccggg aagctagagt aagtagttcg ccagttaata gtttgcgcaa cgttgttggc      3540
attgctacag catcgtggt gtcacgctcg tcgtttggta tggcttcatt cagctccggt       3600
tcccaacgat caaggcgagt tacatgatcc cccatgttgt gcaaaaaagc ggttagctcc      3660
ttcggtcctc cgatcgttgt cagaagtaag ttggccgcag tgttatcact catggttatg      3720
gcagcactgc ataattctct tactgtcatg ccatccgtaa gatgcttttc tgtgactggt      3780
gagtactcaa ccaagtcatt ctgagaatac cgcgcccggc gaccgagttg ctcttgcccg      3840
gcgtcaatac gggataatag tgtatgacat agcagaactt taaaagtgct catcattgga     3900
aaacgttctt cggggcgaaa actctcaagg atcttaccgc tgttgagatc cagttcgatg     3960
taacccactc gtgcacccaa ctgatcttca gcatctttta ctttcaccag cgtttctggg     4020
tgagcaaaaa caggaaggca aaatgccgca aaaaagggaa taaggcgac acggaaatgt      4080 tgaatactca tactcttcct ttttcaatat tattgaagca tttatcaggg ttattgtctc      4140
```

-continued

```
atgagcggat acatatttga atgtatttag aaaaataaac aaatagggt tccgcgcaca    4200 tttccccgaa aagtgccacc tgacgtctaa gaaaccatta ttatcatgac attaacctat   4260
aaaaataggc gtatcacgag gccctttcgt ctcgcgcgtt tcggtgatga cggtgaaaac   4320
ctctgacaca tgcagctccc ggagacggtc acagcttgtc tgtaagcgga tgccgggagc   4380
agacaagccc gtcagggcgc gtcagcgggt gttggcgggt gtcggggctg gcttaactat   4440
gcggcatcag agcagattgt actgagagtg caccatatgc ggtgtgaaat accgcacaga   4500
tgcgtaagga gaaaataccg catcaggcga aattgtaaac gttaatattt tgttaaaatt   4560
cgcgttaaat atttgttaaa tcagctcatt ttttaaccaa taggccgaaa tcggcaaaat   4620
cccttataaa tcaaagaat agaccgagat agggttgagt gttgttccag tttggaacaa   4680
gagtccacta ttaagaacg tggactccaa cgtcaaaggg cgaaaaccg tctatcaggg    4740 cgatggccca ctacgtgaac catcacccaa atcaagtttt ttgcggtcga ggtgccgtaa   4800
agctctaaat cggaaccctca agggagccc ccgatttaga gcttgacggg gaaagccggc    4860
gaacgtggcg agaaggaag ggaagaaagc gaaggagcg ggcgctaggg cgctggcaag     4920
tgtagcggtc acgctgcgcg taaccaccac acccgccgcg cttaatgcgc cgctacaggg   4980
cgcgtccatt cgccattcag gctgcgcaac tgttgggaag ggcgatcggt gcgggcctct   5040
tcgctattac gccagctggc gaaaggggga tgtgctgcaa ggcgattaag ttgggtaacg   5100
ccagggtttt cccagtcacg acgttgtaaa acgacggcca gtgaattg              5148
```

```
<210> SEQ ID NO 11
<211> LENGTH:  3715
<212> TYPE: DNA
<213> ORGANISM: Artificial Sequence
<220> FEATURE:
<223> OTHER INFORMATION: Description of Artificial Sequence: Plasmid
                        TopoRNAi

<400> SEQUENCE: 11
```

```
gagtgcacca tatgcggtgt gaaataccgc acagatgcgt aaggagaaaa taccgcatca     60
ggcgaaattg taaacgttaa tattttgtta aaattcgcgt taaatatttg ttaaatcagc    120 tcattttta accataggc cgaaatcggc aaaatccctt ataaatcaaa agaatagacc      180
gagatagggt tgagtgttgt tccagtttgg aacaagagtc cactattaaa gaacgtggac    240
tccaacgtca aagggcgaaa aaccgtctat caggcgatg ccccactacg tgaaccatca     300
cccaaatcaa gttttttgcg gtcgaggtgc cgtaaagctc taaatcggaa ccctaaaggg    360 agccccgat ttagagcttg acgggaaag ccggcgaacg tggcgagaaa ggaagggaag      420
aaagcgaaag gagcgggcgc tagggcgctg gcaagtgtag cggtcacgct gcgcgtaacc    480
accacccccg ccgcgcttaa tgcgccgcta cagggcgcgt ccattcgcca ttcaggctgc    540
gcaactgttg gaagggcga tcggtgcggg cctcttcgct attacgccag ctggcgaaag    600
ggggatgtgc tgcaaggcga ttaagttggg taacgccagg ttttccag tcacgacgtt     660 gtaaaacgac ggccagtgaa ttgtaatacg actcactata gggcgaattc aaaaaacccc    720
tcaagacccg tttagaggcc ccaagggtt atgctagtga attctgcagg gtacccgggg    780
atcctctaga gatccctcga cctcgagatc cattgtggtg gaattctacc aaggctagca    840
tgggcagccg aatacagtga tccgtgccgg ccctggactg ttgaacgagg tcggcgtaga    900
cggtctgacg acacgcaaac tggcggaacg gttgggggtg cagcagccgg cgctttactg    960
gcacttcagg aacaagcggg cgctgctcga cgcactggcc gaagccatgc tggcggagaa   1020
```

-continued

```
tcatacgctt cggtgccgag agccgacgac gactggcgct catttctgat cgggaatccc    1080
gcagccatgc tagccttggt agaattccac cacaatggat ctcgagggat cttccatacc    1140
taccagttct gcgcctgcag gtcgcggccg cgactctcta gacgcgtaag cttactagca    1200
taaccccttg gggcctctaa acgggtcttg aggggttttt tgagcttctc gccctatagt    1260
gagtcgtatt acagcttgag tattctatag tgtcacctaa atagcttggc gtaatcatgg    1320
tcatagctgt ttcctgtgtg aaattgttat ccgctcacaa ttccacacaa catacgagcc    1380
ggaagcataa agtgtaaagc ctggggtgcc taatgagtga gctaactcac attaattgcg    1440
ttgcgctcac tgcccgcttt ccagtcggga acctgtcgt gccagctgca ttaatgaatc     1500
ggccaacgcg cggggagagg cggtttgcgt attgggcgct cttccgcttc ctcgctcact    1560
gactcgctgc gctcggtcgt tcggctgcgg cgagcggtat cagctcactc aaaggcggta    1620
atacggttat ccacagaatc aggggataac gcaggaaaga acatgtgagc aaaaggccag    1680
caaaaggcca ggaaccgtaa aaaggccgcg ttgctggcgt ttttcgatag gctccgcccc    1740
cctgacgagc atcacaaaaa tcgacgctca agtcagaggt ggcgaaaccc gacaggacta    1800
taaagatacc aggcgtttcc ccctggaagc tccctcgtgc gctctcctgt tccgaccctg    1860
ccgcttaccg gatacctgtc cgcctttctc ccttcgggaa gcgtggcgct ttctcatagc    1920
tcacgctgta ggtatctcag ttcggtgtag gtcgttcgct ccaagctggg ctgtgtgcac    1980
gaaccccccg ttcagcccga ccgctgcgcc ttatccggta actatcgtct tgagtccaac    2040
ccggtaagac acgacttatc gccactggca gcagccactg gtaacaggat tagcagagcg    2100
aggtatgtag gcggtgctac agagttcttg aagtggtggc ctaactacgg ctacactaga    2160
aggacagtat ttggtatctg cgctctgctg aagccagtta ccttcggaaa aagagttggt    2220
agctcttgat ccggcaaaca aaccaccgct ggtagcggtg gttttttgt ttgcaagcag     2280
cagattacgc gcagaaaaaa aggatctcaa gaagatcctt tgatctttc tacggggtct     2340
gacgctcagt ggaacgaaaa ctcacgttaa gggattttgg tcatgagatt atcaaaaagg    2400
atcttcacct agatcctttt aaattaaaaa tgaagtttta aatcaatcta agtatatat     2460
gagtaaactt ggtctgacag ttaccaatgc ttaatcagtg aggcacctat ctcagcgatc    2520
tgtctatttc gttcatccat agttgcctga ctccccgtcg tgtagataac tacgatacgg    2580
gagggcttac catctggccc cagtgctgca atgataccgc gagacccacg ctcaccggct    2640
ccagatttat cagcaataaa ccagccagcc ggaagggccg agcgcagaag tggtcctgca    2700
actttatccg cctccatcca gtctattaat tgttgccggg aagctagagt aagtagttcg    2760
ccagttaata gtttgcgcaa cgttgttggc attgctacag gcatcgtggt gtcacgctcg    2820
tcgtttggta tggcttcatt cagctccggt tcccaacgat caaggcgagt tacatgatcc    2880
cccatgttgt gcaaaaaagc ggttagctcc ttcggtcctc cgatcgttgt cagaagtaag    2940
ttggccgcag tgttatcact catggttatg gcagcactgc ataattctct tactgtcatg    3000
ccatccgtaa gatgcttttc tgtgactggt gagtactcaa ccaagtcatt ctgagaatac    3060
cgcgccggc gaccgagttg ctcttgcccg gcgtcaatac gggataatag tgtatgacat     3120
agcagaactt taaaagtgct catcattgga aaacgttctt cggggcgaaa actctcaagg    3180
atcttaccgc tgttgagatc cagttcgatg taacccactc gtgcacccaa ctgatcttca    3240
gcatctttta ctttcaccag cgtttctggg tgagcaaaaa caggaaggca aaatgccgca    3300
aaaaagggaa taagggcgac acggaaatgt tgaatactca tactcttcct ttttcaatat    3360
```

```
tattgaagca tttatcaggg ttattgtctc atgagcggat acatatttga atgtatttag    3420
aaaaataaac aaatagggt tccgcgcaca tttcccgaa aagtgccacc tgacgtctaa     3480
gaaaccatta ttatcatgac attaacctat aaaaataggc gtatcacgag gccctttcgt    3540
ctcgcgcgtt tcggtgatga cggtgaaaac ctctgacaca tgcagctccc ggagacggtc    3600
acagcttgtc tgtaagcgga tgccgggagc agacaagccc gtcagggcgc gtcagcgggt    3660
gttggcgggt gtcggggctg gcttaactat gcggcatcag agcagattgt actga         3715

<210> SEQ ID NO 12
<211> LENGTH: 4107
<212> TYPE: DNA
<213> ORGANISM: Artificial Sequence
<220> FEATURE:
<223> OTHER INFORMATION: Description of Artificial Sequence: Plasmid
      pGN49A

<400> SEQUENCE: 12
tgtaatacga ctcactatag ggcgaattca aaaaccccct caagaccccgt ttagaggccc      60 caaggggtta tgctagtgaa ttctgcagcg gtacccgggg atcctctaga gatccctcga    120
cctcgagatc cattgtgctg gaaaggatct ggatccggct tactaaaagc cagataacag    180
tatgcgtatt tgcgcgctga tttttgcggt ataagaatat atactgatat gtataccga     240 agtatgtcaa aaagaggtgt gctatgaagc agcgtattac agtgacagtt gacagcgaca    300
gctatcagtt gctcaaggca tatatgatgt caatatctcc ggtctggtaa gcacaaccat    360
gcagaatgaa gcccgtcgtc tgcgtgccga acgctggaaa gcggaaaatc aggaagggat    420
ggctgaggtc gcccggttta ttgaaatgaa cggctctttt gctgacgaga cagggactg    480 gtgaaatgca gtttaaggtt tacacctata aagagagag ccgttatcgt ctgtttgtgg    540
atgtacagag tgatattatt gacacgcccg gcgacggat ggtgatcccc ctggccagtg    600
cacgtctctt aagcgataaa gtctcccgtg aactttaccc ggtggtgcat atcggggatg    660
aaagctggcg catgatgacc accgatatgg ccagtgtgcc ggtctccgtt atcggggaag    720
aagtggctga tctcagccac cgcgaaaatg acatcaaaaa cgccattaac ctgatgttct    780
ggggaatata aatgtcaggc tcccttatac acagcctttc cagcacaatg gatctcgagg    840
gatcttccat acctaccagt tctgcgcctg caggtcgcgg ccgcgactct agacgcgtaa    900
gcttactagc ataacccctt ggggcctcta acgggtctt gaggggtttt ttgagcttct    960
cgccctatag tgagtcgtat tacagcttga gtattctata gtgtcaccta atagcttgg    1020 cgtaatcatg gtcatagctg tttcctgtgt gaaattgtta tccgctcaca attccacaca   1080
acatacgagc cggaagcata aagtgtaaag cctggggtgc ctaatgagtg agctaactca   1140
cattaattgc gttgcgctca ctgcccgctt tccagtcggg aaacctgtcg tgccagctgc   1200
attaatgaat cggccaacgc gcggggagag cggtttgcg tattgggcgc tcttccgctt   1260
cctcgctcac tgactcgctg cgctcggtcg ttcggctgcg gcgagcggta tcagctcact   1320
caaaggcggt aatacggtta tccacagaat caggggataa cgcaggaaag aacatgtgag   1380
caaaaggcca gcaaaaggcc aggaaccgta aaaaggccgc gttgctggcg ttttcgata   1440 ggctccgccc cctgacgag catcacaaaa atcgacgctc aagtcagagg tggcgaaacc   1500
cgacaggact ataaagatac caggcgtttc ccctggaag ctccctcgtg cgctctcctg   1560
ttccgaccct gccgcttacc ggatacctgt ccgcctttct cccttcggga agcgtggcgc   1620
tttctcatag ctcacgctgt aggtatctca gttcggtgta ggtcgttcgc tccaagctgg   1680
```

```
gctgtgtgca cgaacccccc gttcagcccg accgctgcgc cttatccggt aactatcgtc    1740
ttgagtccaa cccggtaaga cacgacttat cgccactggc agcagccact ggtaacagga    1800
ttagcagagc gaggtatgta ggcggtgcta cagagttctt gaagtggtgg cctaactacg    1860
gctacactag aaggacagta tttggtatct gcgctctgct aagccagtt accttcggaa     1920 aaagagttgg tagctcttga tccggcaaac aaaccaccgc tggtagcggt ggttttttg     1980 tttgcaagca gcagattacg cgcagaaaaa aaggatctca agaagatcct ttgatctttt    2040
ctacggggtc tgacgctcag tggaacgaaa actcacgtta agggattttg gtcatgagat    2100
tatcaaaaag gatcttcacc tagatccttt taaattaaaa atgaagtttt aaatcaatct    2160
aaagtatata tgagtaaact tggtctgaca gttaccaatg cttaatcagt gaggcaccta    2220
tctcagcgat ctgtctattt cgttcatcca tagttgcctg actccccgtc gtgtagataa    2280
ctacgatacg ggagggctta ccatctggcc ccagtgctgc aatgataccg cgagacccac    2340
gctcaccggc tccagattta tcagcaataa accagccagc cggaagggcc gagcgcagaa    2400
gtggtcctgc aactttatcc gcctccatcc agtctattaa ttgttgccgg gaagctagag    2460
taagtagttc gccagttaat agtttgcgca acgttgttgg cattgctaca ggcatcgtgg    2520
tgtcacgctc gtcgtttggt atggcttcat tcagctccgg ttcccaacga tcaaggcgag    2580
ttacatgatc ccccatgttg tgcaaaaaag cggttagctc cttcggtcct ccgatcgttg    2640
tcagaagtaa gttggccgca gtgttatcac tcatggttat ggcagcactg cataattctc    2700
ttactgtcat gccatccgta agatgctttt ctgtgactgg tgagtactca accaagtcat    2760
tctgagaata ccgcgcccgg cgaccgagtt gctcttgccc ggcgtcaata cgggataata    2820
gtgtatgaca tagcagaact ttaaaagtgc tcatcattgg aaaacgttct cgggggcgaa    2880
aactctcaag gatcttaccg ctgttgagat ccagttcgat gtaacccact cgtgcaccca    2940
actgatcttc agcatctttt actttcacca gcgtttctgg gtgagcaaaa acaggaaggc    3000
aaaatgccgc aaaaaaggga ataagggcga cacggaaatg ttgaatactc atactcttcc    3060
tttttcaata ttattgaagc atttatcagg gttattgtct catgagcgga tacatatttg    3120
aatgtattta gaaaaataaa caaatagggg ttccgcgcac atttccccga aaagtgccac    3180
ctgacgtcta agaaaccatt attatcatga cattaaccta taaaaatagg cgtatcacga    3240
ggccctttcg tctcgcgcgt ttcggtgatg acggtgaaaa cctctgacac atgcagctcc    3300
cggagacggt cacagcttgt ctgtaagcgg atgccgggag cagacaagcc cgtcagggcg    3360
cgtcagcggg tgttggcggg tgtcggggct ggcttaacta tgcggcatca gagcagattg    3420
tactgagagt gcaccatatg cggtgtgaaa taccgcacag atgcgtaagg agaaaatacc    3480
gcatcaggcg aaattgtaaa cgttaatatt ttgttaaaat tcgcgttaaa tatttgttaa    3540
atcagctcat tttttaacca ataggccgaa atcggcaaaa tcccttataa atcaaaagaa    3600
tagaccgaga tagggttgag tgttgttcca gtttggaaca agagtccact attaaagaac    3660
gtggactcca acgtcaaagg gcgaaaaacc gtctatcagg gcgatggccc actacgtgaa    3720
ccatcaccca atcaagtttt ttgcggtcg aggtgccgta aagctctaaa tcggaaccct    3780
aaagggagcc ccgatttag agcttgacgg ggaaagccgg cgaacgtggc gagaaaggaa    3840
gggaagaaag cgaaaggagc gggcgctagg gcgctggcaa gtgtagcggt cacgctgcgc    3900
gtaaccacca cacccgccgc gcttaatgcg ccgctacagg gcgcgtccat tcgccattca    3960
ggctgcgcaa ctgttgggaa gggcgatcgg tgcgggcctc ttcgctatta cgccagctgg    4020
cgaaaggggg atgtgctgca aggcgattaa gttgggtaac gccagggttt tcccagtcac    4080
```

-continued

```
gacgttgtaa aacgacggcc agtgaat                                      4107
```

<210> SEQ ID NO 13
<211> LENGTH: 4001
<212> TYPE: DNA
<213> ORGANISM: Artificial Sequence
<220> FEATURE:
<223> OTHER INFORMATION: Description of Artificial Sequence: Plasmid pGN59A

<400> SEQUENCE: 13

```
gagtgcacca tatgcggtgt gaaataccgc acagatgcgt aaggagaaaa taccgcatca    60
ggcgaaattg taaacgttaa tattttgtta aaattcgcgt taaatatttg ttaaatcagc   120
tcattttta accataggc cgaaatcggc aaaatccctt ataaatcaaa agaatagacc   180
gagatagggt tgagtgttgt tccagtttgg aacaagagtc cactattaaa gaacgtggac   240
tccaacgtca aagggcgaaa aaccgtctat cagggcgatg gcccactacg tgaaccatca   300
cccaaatcaa gttttttgcg gtcgaggtgc cgtaaagctc taaatcggaa ccctaaaggg   360
agcccccgat ttagagcttg acggggaaag ccggcgaacg tggcgagaaa ggaagggaag   420
aaagcgaaag gagcgggcgc tagggcgctg gcaagtgtag cggtcacgct gcgcgtaacc   480
accacaccg ccgcgcttaa tgcgccgcta cagggcgcgt ccattcgcca ttcaggctgc   540
gcaactgttg ggaagggcga tcggtgcggg cctcttcgct attacgccag ctggcgaaag   600
ggggatgtgc tgcaaggcga ttaagttggg taacgccagg gttttcccag tcacgacgtt   660
gtaaaacgac ggccagtgaa ttgtaatacg actcactata gggcgaattc gagctcggta   720
cccggggatc ctctagagat ccctcgacct cgagatccat tgtgctggaa aggatctgga   780
tccggcttac taaaagccag ataacagtat gcgtatttgc gcgctgattt ttgcggtata   840
agaatatata ctgatatgta tacccgaagt atgtcaaaaa gaggtgtgct atgaagcagc   900
gtattacagt gacagttgac agcgacagct atcagttgct caaggcatat atgatgtcaa   960
tatctccggt ctggtaagca caaccatgca gaatgaagcc cgtcgtctgc gtgccgaacg  1020
ctggaaagcg gaaaatcagg aagggatggc tgaggtcgcc cggtttattg aaatgaacgg  1080
ctcttttgct gacgagaaca gggactggtg aaatgcagtt taaggtttac acctataaaa  1140
gagagagccg ttatcgtctg tttgtggatg tacagagtga tattattgac acgcccgggc  1200
gacggatggt gatcccctg ccagtgcac gtctcttaag cgataaagtc tcccgtgaac  1260
tttacccggt ggtgcatatc ggggatgaaa gctggcgcat gatgaccacc gatatggcca  1320
gtgtgccggt ctccgttatc ggggaagaag tggctgatct cagccaccgc gaaaatgaca  1380
tcaaaaacgc cattaacctg atgttctggg gaatataaat gtcaggctcc cttatacaca  1440
gccttccag cacaatggat ctcgagggat cttccatacc taccagttct gcgcctgcag  1500
gtcgcggccg cgactctcta gagtcgaaag cttctcgccc tatagtgagt cgtattacag  1560
cttgagtatt ctatagtgtc acctaaatag cttggcgtaa tcatggtcat agctgtttcc  1620
tgtgtgaaat tgttatccgc tcacaattcc acacaacata cgagccggaa gcataaagtg  1680
taaagcctgg ggtgcctaat gagtgagcta actcacatta attgcgttgc gctcactgcc  1740
cgctttccag tcgggaaacc tgtcgtgcca gctgcattaa tgaatcggcc aacgcgcggg  1800
gagaggcggt ttgcgtattg ggcgctcttc cgcttcctcg ctcactgact cgctgcgctc  1860
ggtcgttcgg ctgcggcgag cggtatcagc tcactcaaag gcggtaatac ggttatccac  1920
agaatcaggg gataacgcag gaaagaacat gtgagcaaaa ggccagcaaa aggccaggaa  1980
```

-continued

```
ccgtaaaaag gccgcgttgc tggcgttttt cgataggctc cgccccctg acgagcatca      2040 caaaaatcga cgctcaagtc agaggtggcg aaacccgaca ggactataaa gataccaggc      2100
gtttccccct ggaagctccc tcgtgcgctc tcctgttccg accctgccgc ttaccggata      2160
cctgtccgcc tttctccctt cgggaagcgt ggcgctttct catagctcac gctgtaggta      2220
tctcagttcg gtgtaggtcg ttcgctccaa gctgggctgt gtgcacgaac cccccgttca      2280
gcccgaccgc tgcgccttat ccggtaacta tcgtcttgag tccaacccgg taagacacga      2340
cttatcgcca ctggcagcag ccactggtaa caggattagc agagcgaggt atgtaggcgg      2400
tgctacagag ttcttgaagt ggtggcctaa ctacggctac actagaagga cagtatttgg      2460
tatctgcgct ctgctgaagc cagttacctt cggaaaaaga gttggtagct cttgatccgg      2520
caaacaaacc accgctggta gcggtggttt ttttgtttgc aagcagcaga ttacgcgcag      2580
aaaaaaagga tctcaagaag atcctttgat cttttctacg gggtctgacg ctcagtggaa      2640
cgaaaactca cgttaaggga ttttggtcat gagattatca aaaaggatct tcacctagat      2700
ccttttaaat taaaaatgaa gttttaaatc aatctaaagt atatatgagt aaacttggtc      2760
tgacagttac caatgcttaa tcagtgaggc acctatctca gcgatctgtc tatttcgttc      2820
atccatagtt gcctgactcc ccgtcgtgta gataactacg atacgggagg gcttaccatc      2880
tggccccagt gctgcaatga taccgcgaga cccacgctca ccggctccag atttatcagc      2940
aataaaccag ccagccggaa gggccgagcg cagaagtggt cctgcaactt tatccgcctc      3000
catccagtct attaattgtt gccgggaagc tagagtaagt agttcgccag ttaatagttt      3060
gcgcaacgtt gttggcattg ctacaggcat cgtggtgtca cgctcgtcgt ttggtatggc      3120
ttcattcagc tccggttccc aacgatcaag gcgagttaca tgatccccca tgttgtgcaa      3180
aaaagcggtt agctccttcg gtcctccgat cgttgtcaga agtaagttgg ccgcagtgtt      3240
atcactcatg gttatggcag cactgcataa ttctcttact gtcatgccat ccgtaagatg      3300
cttttctgtg actggtgagt actcaaccaa gtcattctga ataccgcg cccggcgacc       3360 gagttgctct tgcccggcgt caatacggga taatagtgta tgacatagca gaactttaaa      3420
agtgctcatc attggaaaac gttcttcggg gcgaaaactc tcaaggatct taccgctgtt      3480
gagatccagt tcgatgtaac ccactcgtgc acccaactga tcttcagcat cttttacttt      3540
caccagcgtt tctgggtgag caaaaacagg aaggcaaaat gccgcaaaaa agggaataag      3600
ggcgacacgg aaatgttgaa tactcatact cttcctttt caatattatt gaagcattta       3660
tcagggttat tgtctcatga gcggatacat atttgaatgt atttagaaaa ataaacaaat      3720
aggggttccg cgcacatttc cccgaaaagt gccacctgac gtctaagaaa ccattattat      3780
catgacatta acctataaaa ataggcgtat cacgaggccc tttcgtctcg cgcgtttcgg      3840
tgatgacggt gaaaacctct gacacatgca gctcccggag acggtcacag cttgtctgta      3900
agcggatgcc gggagcagac aagcccgtca gggcgcgtca gcgggtgttg gcgggtgtcg      3960
gggctggctt aactatgcgg catcagagca gattgtactg a                          4001
```

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide oGN103

<400> SEQUENCE: 14

-continued taccaaggct agcatggttt atcactgata agttgg        36

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence:
      Olgigonucleotide oGN104

<400> SEQUENCE: 15
taccaaggct agcatgggcc tgcctgaagg ctgc        34

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide oGN126

<400> SEQUENCE: 16
gatctggatc cggcttacta aaagccagat aacagtatgc        40

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence:
      Oligonucleotide oGN127

<400> SEQUENCE: 17
ggagacttta tcgcttaaga gacgtgcact ggccaggggg atcacc        46

<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide oGN128

<400> SEQUENCE: 18
ccagtgcacg tctcttaagc gataaagtct cccgtgaact ttacccggtg g        51

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide oGN129

<400> SEQUENCE: 19
gctgtgtata agggagcctg acatttatat tccccag        37

<210> SEQ ID NO 20
<211> LENGTH: 375
<212> TYPE: DNA
<213> ORGANISM: Artificial Sequence
<220> FEATURE:
<223> OTHER INFORMATION: Description of Artificial Sequence: PCR
      fragment generated by primers oGN103 and 0GN104
      on pCDM8

<400> SEQUENCE: 20

```
taccaaggct agcatggttt atcactgata agttggataa gttggtggac atattatgtt      60
tatcagtgat aaagtgtcaa gcatgacaaa gttgcagccg aatacagtga tccgtgccgg     120
ccctggactg ttgaacgagg tcggcgtaga cggtctgacg acacgcaaac tggcggaacg     180
gttgggggtg cagcagccgg cgctttactg gcacttcagg aacaagcggg cgctgctcga     240
cgcactggcc gaagccatgc tggcggagaa tcatacgctt cggtgccgag agccgacgac     300
gactggcgct catttctgat cgggaatccc gcagcttcag gcaggcccat gctagccttg     360
gtaccagcac aatgg                                                     375

<210> SEQ ID NO 21
<211> LENGTH: 670
<212> TYPE: DNA
<213> ORGANISM: Artificial Sequence
<220> FEATURE:
<223> OTHER INFORMATION: Description of Artificial Sequence: PCR
                        fragment

<400> SEQUENCE: 21
gatctggatc cggcttacta aaagccagat aacagtatgc gtatttgcgc gctgattttt      60
gcggtataag aatatatact gatatgtata cccgaagtat gtcaaaaaga ggtgtgctat     120
gaagcagcgt attacagtga cagttgacag cgacagctat cagttgctca aggcatatat     180
gatgtcaata tctccggtct ggtaagcaca accatgcaga atgaagcccg tcgtctgcgt     240
gccgaacgct ggaaagcgga aaatcaggaa gggatggctg aggtcgcccg gtttattgaa     300
atgaacggct cttttgctga cgagaacagg gactggtgaa atgcagttta aggtttacac     360
ctataaaaga gagagccgtt atcgtctgtt tgtggatgta cagagtgata ttattgacac     420
gcccgggcga cggatggtga tccccctggc cagtgcacgt ctcttaagcg ataaagtctc     480
ccgtgaactt tacccggtgg tgcatatcgg ggatgaaagc tggcgcatga tgaccaccga     540
tatggccagt gtgccggtct ccgttatcgg ggaagaagtg gctgatctca gccaccgcga     600
aaatgacatc aaaaacgcca ttaacctgat gttctgggga atataaatgt caggctccct     660
tatacacagc                                                           670
```